(12) United States Patent
Murray et al.

(10) Patent No.: US 9,788,861 B2
(45) Date of Patent: Oct. 17, 2017

(54) EXTERNAL BONE FIXATION DEVICE

(71) Applicant: DePuy Synthes Products, Inc., Raynham, MA (US)

(72) Inventors: Nicole Murray, West Milford, NJ (US); Michael Wahl, West Chester, PA (US); Jean-Noel Bordeaux, West Chester, PA (US); Thomas Joseph Maughan, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/691,683

(22) Filed: Apr. 21, 2015

(65) Prior Publication Data

US 2015/0223842 A1 Aug. 13, 2015

Related U.S. Application Data

(62) Division of application No. 13/800,319, filed on Mar. 13, 2013, now Pat. No. 9,039,706.

(51) Int. Cl.
*A61B 17/00* (2006.01)
*A61B 17/62* (2006.01)
*A61B 17/60* (2006.01)

(52) U.S. Cl.
CPC ........ *A61B 17/62* (2013.01); *A61B 2017/606* (2013.01)

(58) Field of Classification Search
CPC ..... A61B 17/62; A61B 17/66; A61B 17/6466; A61B 17/6416; A61B 17/645; A61B 17/6458; A61B 17/60; A61B 17/6425; A61B 17/6433; A61B 17/6441; A61B 17/64; A61B 17/6475; A61B 2017/606; A61B 17/6491

USPC ..................................... 606/53-59
See application file for complete search history.

(56) References Cited

U.S. PATENT DOCUMENTS

| | | | |
|---|---|---|---|
| 2,055,024 A | 9/1936 | Bittner et al. |
| 2,391,537 A | 12/1945 | Anderson |
| 3,977,397 A | 8/1976 | Kalnberz et al. |
| 4,081,686 A | 3/1978 | Nieuweboer |

(Continued)

FOREIGN PATENT DOCUMENTS

| | | |
|---|---|---|
| EP | 1100048 | 5/2001 |
| EP | 1690506 | 8/2006 |

(Continued)

OTHER PUBLICATIONS

Garreau et al., "A Knowledge-Based Approach for 3-D Reconstruction and Labeling of Vascular Networks from Biplane Angiographic Projections", IEEE Transactions on Medical Imaging, Jun. 1991, vol. 10, No. 2, 122-131.

(Continued)

*Primary Examiner* — Eduardo C Robert
*Assistant Examiner* — Tara R Carter
(74) *Attorney, Agent, or Firm* — Baker & Hostetler LLP

(57) ABSTRACT

The present application discloses embodiments related to an external bone fixation device configured to correct bone deformities or repair bone injuries. The device can include a plurality of bases configured to be attached to portions of a bone and a plurality of struts configured to be adjustable in length to change the position and orientation of the plurality of bases and the attached bone portions.

16 Claims, 16 Drawing Sheets

(56) References Cited

U.S. PATENT DOCUMENTS

| | | |
|---|---|---|
| 4,450,834 A | 5/1984 | Fischer |
| 4,615,338 A | 10/1986 | Ilizarov et al. |
| 4,620,533 A | 11/1986 | Mears |
| 4,630,203 A | 12/1986 | Szirtes |
| 4,768,524 A | 9/1988 | Hardy |
| 4,784,125 A | 11/1988 | Monticelli et al. |
| 4,875,165 A | 10/1989 | Fencil et al. |
| 4,889,111 A | 12/1989 | Ben-Dov |
| 4,890,631 A | 1/1990 | Hardy |
| 4,930,961 A | 6/1990 | Weis |
| 4,964,320 A | 10/1990 | Lee, Jr. |
| 4,973,331 A | 11/1990 | Pursley et al. |
| 5,062,844 A | 11/1991 | Jamison et al. |
| 5,074,866 A | 12/1991 | Sherman et al. |
| 5,087,258 A | 2/1992 | Schewior |
| 5,095,919 A | 3/1992 | Monticelli et al. |
| 5,108,393 A | 4/1992 | Ruffa |
| 5,156,605 A | 10/1992 | Pursley et al. |
| 5,179,525 A | 1/1993 | Griffs et al. |
| 5,180,380 A | 1/1993 | Pursley et al. |
| 5,209,750 A | 5/1993 | Stef |
| 5,275,598 A | 1/1994 | Cook |
| 5,358,504 A | 10/1994 | Paley et al. |
| 5,437,668 A | 8/1995 | Aronson et al. |
| 5,443,464 A | 8/1995 | Russell et al. |
| 5,451,225 A | 9/1995 | Ross, Jr. et al. |
| 5,458,599 A | 10/1995 | Adobbati |
| 5,540,686 A | 7/1996 | Zippel et al. |
| 5,601,551 A | 2/1997 | Taylor et al. |
| 5,630,814 A | 5/1997 | Ross, Jr. et al. |
| 5,653,707 A | 8/1997 | Taylor et al. |
| 5,681,309 A | 10/1997 | Ross, Jr. et al. |
| 5,702,389 A | 12/1997 | Taylor et al. |
| 5,728,095 A | 3/1998 | Taylor et al. |
| 5,746,741 A | 5/1998 | Kraus et al. |
| 5,766,173 A | 6/1998 | Ross, Jr. et al. |
| 5,776,132 A | 7/1998 | Blyakher |
| 5,871,018 A | 2/1999 | Delp et al. |
| 5,885,282 A | 3/1999 | Szabo |
| 5,891,143 A | 4/1999 | Taylor et al. |
| 5,919,192 A | 7/1999 | Shouts |
| 5,951,556 A | 9/1999 | Faccioli et al. |
| 5,961,515 A | 10/1999 | Taylor et al. |
| 5,968,043 A | 10/1999 | Ross, Jr. et al. |
| 5,971,984 A | 10/1999 | Taylor et al. |
| 5,976,142 A | 11/1999 | Chin |
| 6,017,341 A | 1/2000 | Windhagen et al. |
| 6,021,579 A | 2/2000 | Schimmels et al. |
| 6,030,386 A | 2/2000 | Taylor et al. |
| 6,047,080 A | 4/2000 | Chen et al. |
| 6,129,727 A | 10/2000 | Austin et al. |
| 6,206,566 B1 | 3/2001 | Schuetz |
| 6,293,947 B1 | 9/2001 | Buchbinder |
| 6,320,928 B1 | 11/2001 | Vaillant et al. |
| 6,363,169 B1 | 3/2002 | Ritter et al. |
| 6,434,278 B1 | 8/2002 | Hashimoto |
| 6,501,848 B1 | 12/2002 | Carroll et al. |
| 6,510,241 B1 | 1/2003 | Vaillant et al. |
| 6,537,275 B2 | 3/2003 | Venturini et al. |
| 6,701,174 B1 | 3/2004 | Krause et al. |
| 6,912,293 B1 | 6/2005 | Korobkin |
| 7,113,623 B2 | 9/2006 | Chen et al. |
| 7,187,792 B2 | 3/2007 | Fu et al. |
| 7,226,449 B2 | 6/2007 | Venturini et al. |
| 7,280,687 B2 | 10/2007 | Ban et al. |
| 7,306,601 B2 | 12/2007 | McGrath et al. |
| 7,388,972 B2 | 6/2008 | Kitson |
| 7,490,085 B2 | 2/2009 | Walker et al. |
| RE40,914 E | 9/2009 | Taylor et al. |
| 7,645,279 B1 | 1/2010 | Haupt |
| 7,657,079 B2 | 2/2010 | Lake et al. |
| 7,677,078 B2 | 3/2010 | Sauer et al. |
| 7,758,582 B2 | 7/2010 | Ferrante et al. |
| 7,828,801 B2 | 11/2010 | Mirza et al. |
| 7,837,621 B2 | 11/2010 | Krause et al. |
| 7,887,537 B2 | 2/2011 | Ferrante et al. |
| 7,955,334 B2 | 6/2011 | Steiner et al. |
| 8,029,505 B2 | 10/2011 | Hearn et al. |
| 8,057,474 B2 | 11/2011 | Knuchel et al. |
| 8,062,293 B2 | 11/2011 | Steiner et al. |
| 8,147,491 B2 | 4/2012 | Lavi |
| 8,157,800 B2 | 4/2012 | Vvedensky et al. |
| 8,202,273 B2 | 6/2012 | Karidis |
| 8,257,353 B2 | 9/2012 | Wong |
| 8,282,652 B2 | 10/2012 | Mackenzi et al. |
| 8,296,094 B2 | 10/2012 | Harrison et al. |
| 8,323,282 B2 | 12/2012 | Taylor |
| 8,333,766 B2 | 12/2012 | Edelhauser et al. |
| 8,377,060 B2 | 2/2013 | Vasta et al. |
| 8,419,732 B2 | 4/2013 | Mullaney |
| 8,425,512 B2 | 4/2013 | Vasta et al. |
| 8,430,878 B2 | 4/2013 | Vasta et al. |
| 8,439,914 B2 | 5/2013 | Ross et al. |
| 8,444,644 B2 | 5/2013 | Ross et al. |
| 8,454,604 B2 | 6/2013 | Wong |
| 8,469,958 B2 | 6/2013 | Stevens |
| 8,574,232 B1 | 11/2013 | Ross et al. |
| 8,654,150 B2 | 2/2014 | Haskell |
| 8,777,946 B2 | 7/2014 | Lindahl et al. |
| 8,834,467 B2 | 9/2014 | Singh et al. |
| 8,864,763 B2 | 10/2014 | Murray et al. |
| 8,906,021 B1 | 12/2014 | Lehmann et al. |
| 8,945,128 B2 | 2/2015 | Singh et al. |
| 8,951,252 B2 | 2/2015 | Steiner et al. |
| 8,952,986 B2 | 2/2015 | Haskell |
| 9,011,438 B2 | 4/2015 | Steiner et al. |
| 9,017,339 B2 | 4/2015 | Edelhauser et al. |
| 9,039,706 B2 | 5/2015 | Murray et al. |
| 9,044,271 B2 | 6/2015 | Edelhauser et al. |
| 9,066,756 B2 | 6/2015 | Wong |
| 9,078,700 B2 | 7/2015 | Ross et al. |
| 9,101,398 B2 | 8/2015 | Singh et al. |
| 9,155,559 B2 | 10/2015 | Ross et al. |
| 9,204,937 B2 | 12/2015 | Edelhauser et al. |
| 9,220,533 B2 | 12/2015 | Singh et al. |
| 2002/0010465 A1 | 1/2002 | Koo et al. |
| 2003/0191466 A1 | 10/2003 | Austin et al. |
| 2004/0039259 A1 | 2/2004 | Krause et al. |
| 2004/0073211 A1 | 4/2004 | Austin et al. |
| 2004/0073212 A1 | 4/2004 | Kim |
| 2004/0097922 A1 | 5/2004 | Mullaney |
| 2004/0111024 A1 | 6/2004 | Zheng et al. |
| 2004/0133199 A1 | 7/2004 | Coati et al. |
| 2004/0167518 A1 | 8/2004 | Estrada |
| 2004/0208279 A1 | 10/2004 | Xiao et al. |
| 2005/0215997 A1 | 9/2005 | Austin et al. |
| 2005/0256389 A1 | 11/2005 | Koga et al. |
| 2006/0276786 A1 | 12/2006 | Brinker |
| 2007/0161984 A1 | 7/2007 | Cresina et al. |
| 2007/0238069 A1 | 10/2007 | Lovald et al. |
| 2008/0012850 A1 | 1/2008 | Keating, III |
| 2008/0051779 A1 | 2/2008 | Mackenzie et al. |
| 2008/0114267 A1 | 5/2008 | Lloyd et al. |
| 2008/0234554 A1 | 9/2008 | Vvedensky et al. |
| 2008/0269741 A1 | 10/2008 | Karidis |
| 2009/0036890 A1 | 2/2009 | Karidis |
| 2009/0036892 A1 | 2/2009 | Karidis et al. |
| 2009/0143788 A1 | 6/2009 | Fang et al. |
| 2009/0161945 A1 | 6/2009 | Morgan-Mar et al. |
| 2009/0177198 A1 | 7/2009 | Theodoros et al. |
| 2009/0198234 A1 | 8/2009 | Knuchel et al. |
| 2009/0226055 A1 | 9/2009 | Dankowicz et al. |
| 2009/0275944 A1 | 11/2009 | Huebner et al. |
| 2010/0030219 A1 | 2/2010 | Lerner et al. |
| 2010/0039421 A1 | 2/2010 | Toyomura et al. |
| 2010/0087819 A1 | 4/2010 | Mullaney |
| 2010/0104150 A1 | 4/2010 | Saint Felix et al. |
| 2010/0172567 A1 | 7/2010 | Prokoski |
| 2010/0191239 A1 | 7/2010 | Sakkers et al. |
| 2010/0191500 A1 | 7/2010 | Harrison et al. |
| 2010/0234844 A1 | 9/2010 | Edelhauser et al. |
| 2010/0280516 A1 | 11/2010 | Taylor |
| 2010/0305568 A1 | 12/2010 | Ross et al. |
| 2010/0312243 A1 | 12/2010 | Ross et al. |

(56) References Cited

U.S. PATENT DOCUMENTS

| | | |
|---|---|---|
| 2011/0004199 A1 | 1/2011 | Ross et al. |
| 2011/0029093 A1 | 2/2011 | Bojarski et al. |
| 2011/0103676 A1 | 5/2011 | Mullaney |
| 2011/0118737 A1 | 5/2011 | Vasta et al. |
| 2011/0118738 A1 | 5/2011 | Vasta et al. |
| 2011/0208187 A1* | 8/2011 | Wong ............... A61B 17/6416 606/59 |
| 2011/0313418 A1 | 12/2011 | Nikonovas |
| 2011/0313419 A1 | 12/2011 | Mullaney |
| 2012/0041439 A1 | 2/2012 | Singh et al. |
| 2012/0078251 A1 | 3/2012 | Benenati et al. |
| 2012/0259343 A1 | 10/2012 | Clark et al. |
| 2012/0303028 A1 | 11/2012 | Wong |
| 2012/0330312 A1 | 12/2012 | Burgherr et al. |
| 2013/0060146 A1 | 3/2013 | Yang et al. |
| 2013/0131675 A1 | 5/2013 | Vasta et al. |
| 2013/0245625 A1 | 9/2013 | Vasta et al. |
| 2013/0289575 A1 | 10/2013 | Edelhauser et al. |
| 2013/0296857 A1 | 11/2013 | Lester |
| 2014/0135764 A1 | 5/2014 | Ross et al. |
| 2014/0257286 A1 | 9/2014 | Lindahl et al. |
| 2014/0278325 A1 | 9/2014 | Burgherr et al. |
| 2014/0379038 A1 | 12/2014 | Dogramadzi et al. |
| 2015/0080892 A1 | 3/2015 | Lehmann et al. |
| 2015/0088135 A1 | 3/2015 | Singh |
| 2015/0112339 A1 | 4/2015 | Lindahl et al. |
| 2015/0223842 A1 | 8/2015 | Murray et al. |
| 2015/0238227 A1 | 8/2015 | Singh et al. |
| 2015/0257788 A1 | 9/2015 | Jay et al. |
| 2015/0265313 A1 | 9/2015 | Wong |
| 2015/0272624 A1 | 10/2015 | Singh |
| 2015/0305776 A1 | 10/2015 | Ross et al. |
| 2015/0305777 A1 | 10/2015 | Singh et al. |
| 2015/0313641 A1 | 11/2015 | Ross et al. |
| 2016/0022314 A1 | 1/2016 | Bordeaux et al. |
| 2016/0045225 A1 | 2/2016 | Edelhauser et al. |
| 2016/0092651 A1 | 3/2016 | Austin et al. |
| 2016/0113681 A1 | 4/2016 | Singh |

FOREIGN PATENT DOCUMENTS

| | | |
|---|---|---|
| FR | 2576774 | 8/1986 |
| FR | 2756025 | 5/1998 |
| JP | 2001-523985 | 11/2001 |
| JP | 2003-144454 | 5/2003 |
| JP | 2003-530177 | 10/2003 |
| JP | 2006-507056 | 3/2006 |
| WO | WO 98/12975 | 4/1998 |
| WO | WO 01/15611 | 3/2001 |
| WO | WO 03/030759 | 4/2003 |
| WO | WO 2007/024904 | 3/2007 |
| WO | WO 2009/102904 | 8/2009 |
| WO | WO 2010/002587 | 1/2010 |
| WO | WO 2010/104567 | 9/2010 |
| WO | WO 2011/026475 | 3/2011 |
| WO | WO 2011/060264 | 5/2011 |
| WO | WO 2011/060266 | 5/2011 |
| WO | WO 2011/146703 A1 | 11/2011 |
| WO | WO 2014/186453 | 11/2014 |

OTHER PUBLICATIONS

Hartley, "Euclidian Reconstruction from Uncalibrated Views", Applications of Invariance in Computer Vision, May 1994, vol. 825, pp. 237-256.

Kelly, "How to Calculate 3-D Coordinates With Two Cameras, A Calibration Object, A Java Program, and a lot of MS Excel Macros", Jun. 10, 2002, 9 pages.

Maiocchi et al., "Operative Principles of Ilizarov", Chapter 2, 1991, 26 pages.

Paley et al., "Deformity Correction by the Ilizarov Technique", Operative Orthopaedics, 1993, 883-948.

Paley, "The Principles of Deformity Correction by the Ilizarov Technique: Technical Aspects", Techniques in Orthopaedics, 1989, vol. 4, Issue 1, 15-29.

Russakoff et al., "Intensity-Based 2D-3D Spine Image Registration Incorporating a Single Fiducial Marker", Academic Radiology, Jan. 2005, vol. 12, No. 1, 37-50.

Simard et al., "The Ilizarov Procedure: Limb Lengthening and It's Implications", Physical Therapy, Jan. 1992, vol. 72, No. 1, 25-35.

Solomin, "The Basic Principles of External Fixation Using the Ilizarov Device", 2005, 371 pages.

Stoughton et al., "A Modified Stewart Platform Manipulator with Improved Dexterity", IEEE Transactions on Robotics and Automation, Apr. 1993, vol. 9, No. 2, 166-173.

Trucco et al., "Introductory Techniques of 3-D Computer Vision", 1998 pp. 178-194.

Tsai, "A Versatile Camera Calibration Technique for High-Accuracy 3-D Machine Vision Metrology Using of-the-shelf TV Cameras and Lenses", IEEE Journal of Robotics & Automation, RA-3, No. 4, Aug. 1987, 323-344.

Viceconti et al., "A Software Simulation of Tibial Fracture Reduction with External Fixator", Computer Methods and Programs in Biomedicine, 1993, 40, 89-94.

Solomin et al., Deformity Correction and Fracture Treatment by Software-Based Ortho-SUV Frame User Manual, 2013, 144 pages.

T.A. Larionova et al. "X-ray absorptiometry in the analysis of bone mineral density of a patient with an orthopaedic trauma", Genius of Orthopaedy No. 3, pp. 98-102 (w/English abstract). 2009.

Decision to Grant (Translation) issued Mar. 2016 in Russian patent application 2012147835, 6 pages.

Orthofix, TL-HEX Software User's Guide: Software version 1.4, Nov. 2015, 60 pages.

* cited by examiner

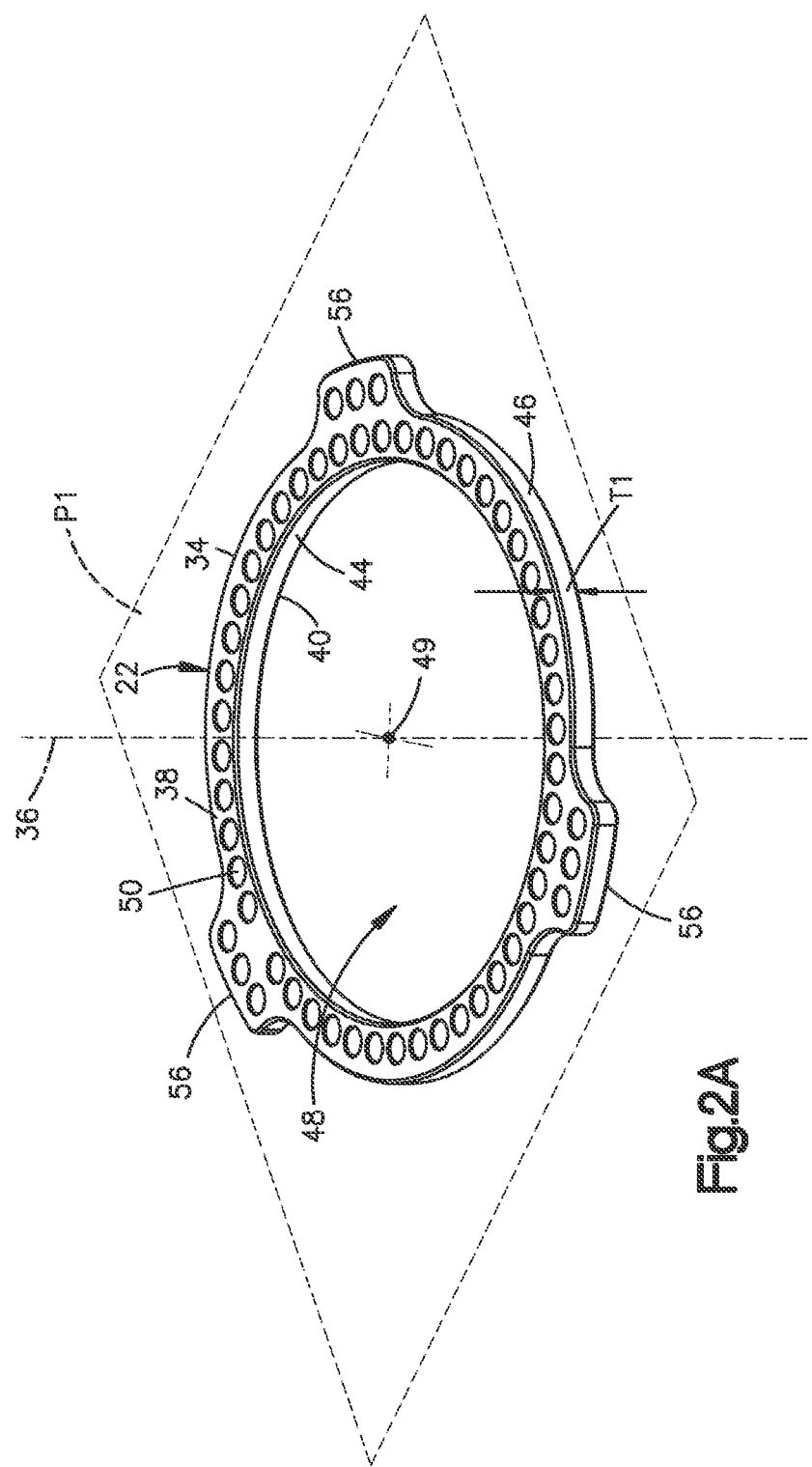

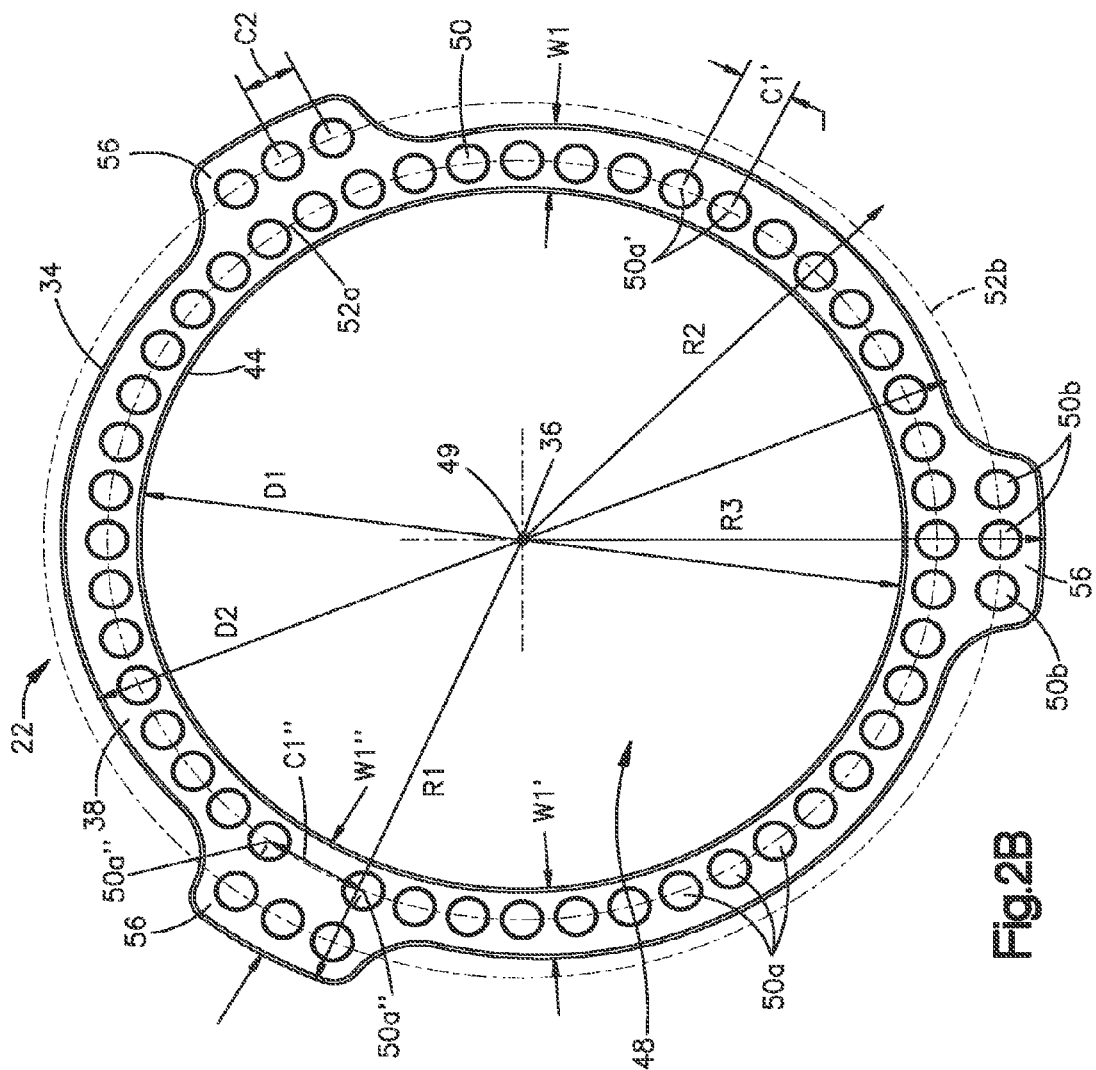

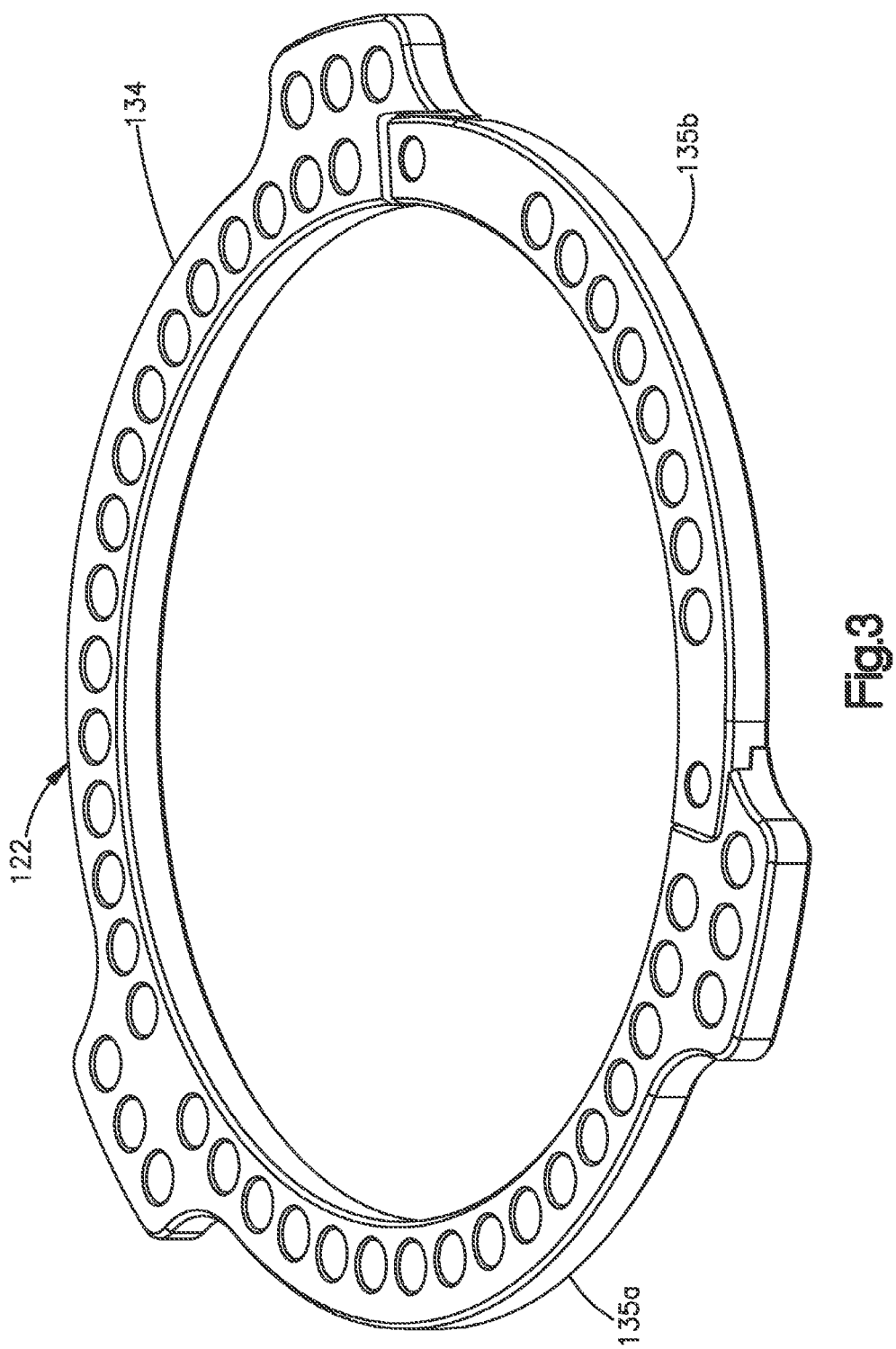

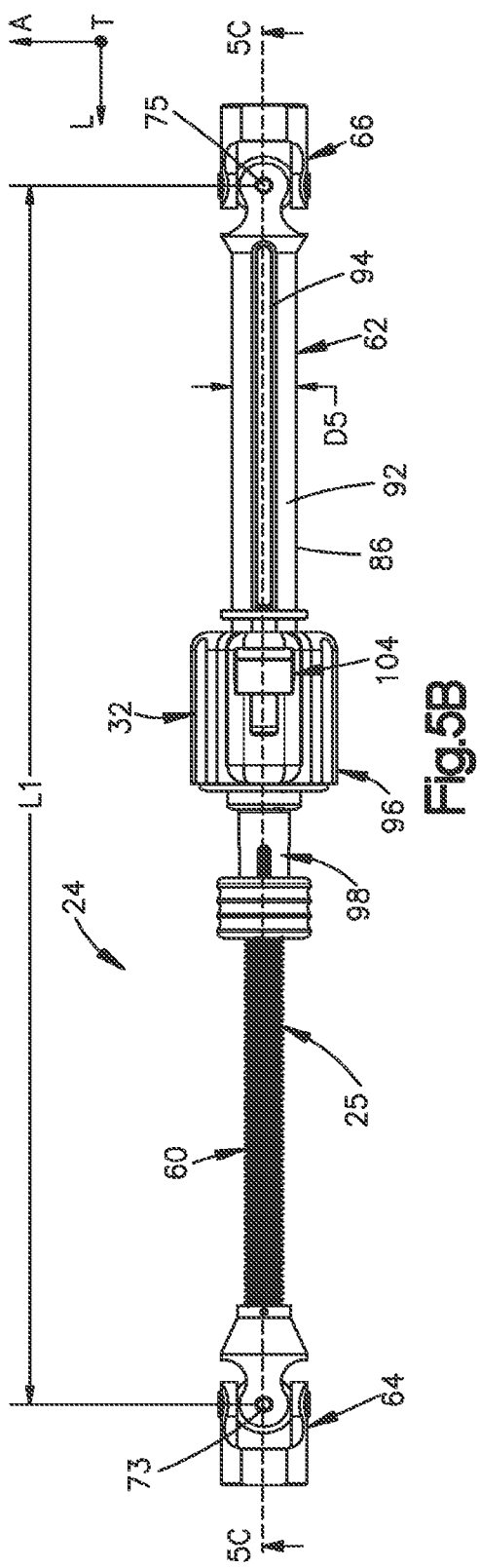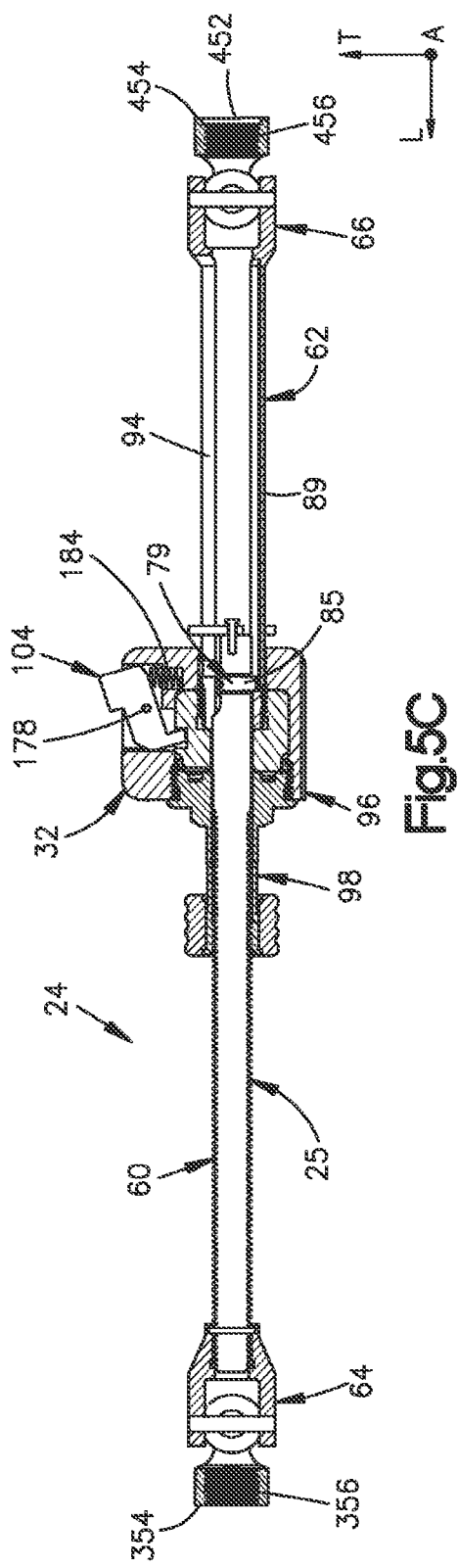

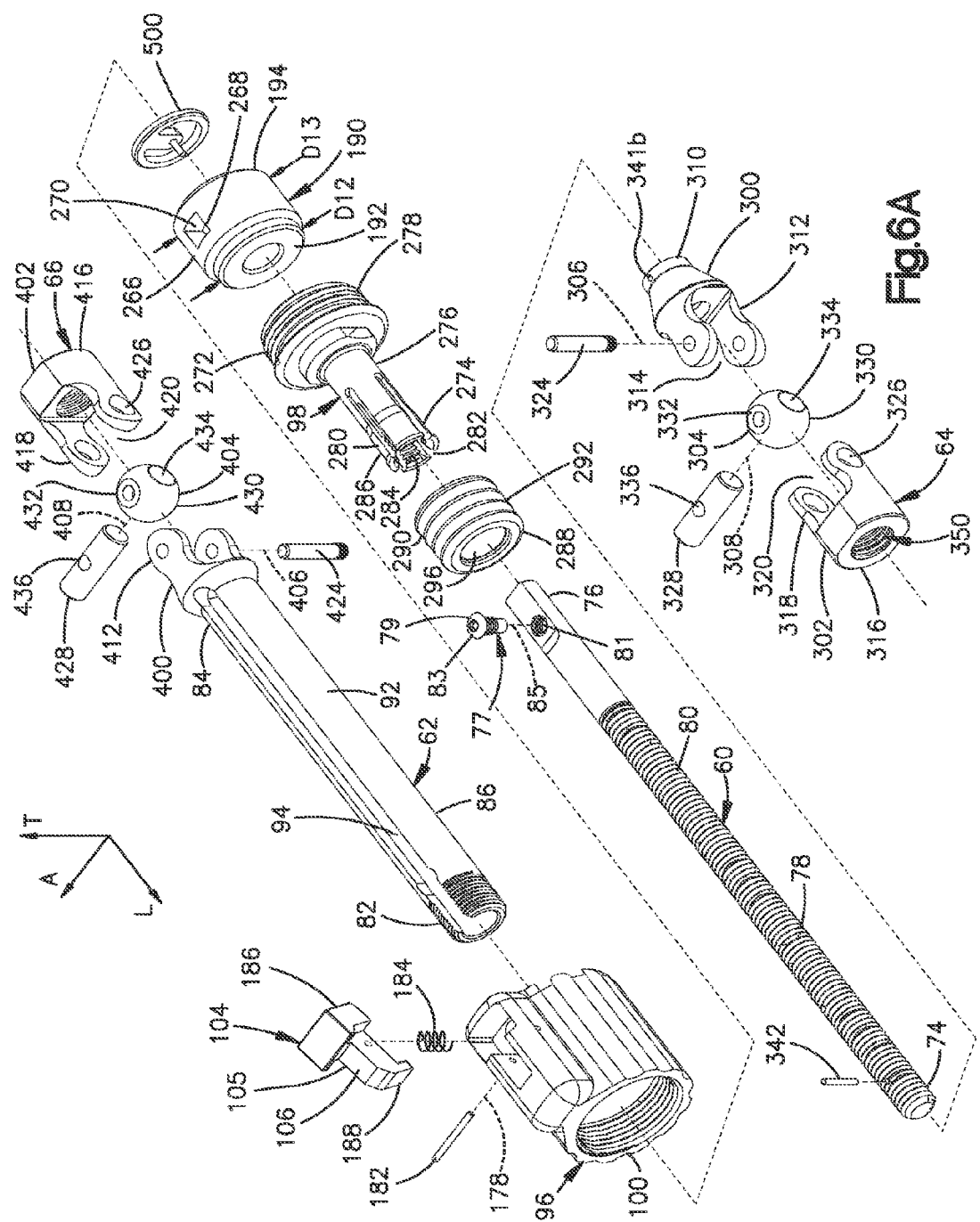

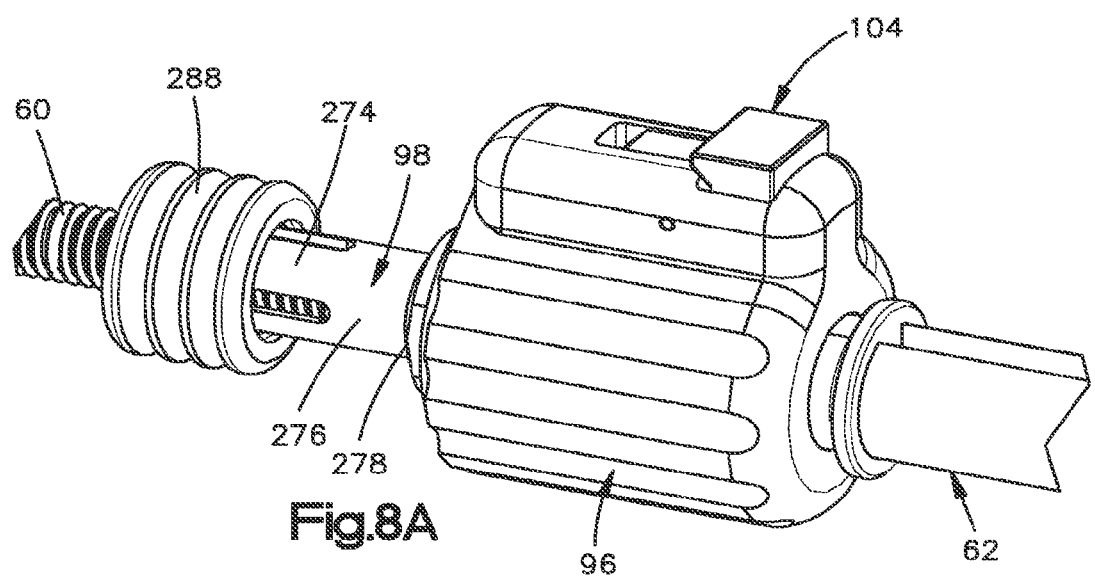
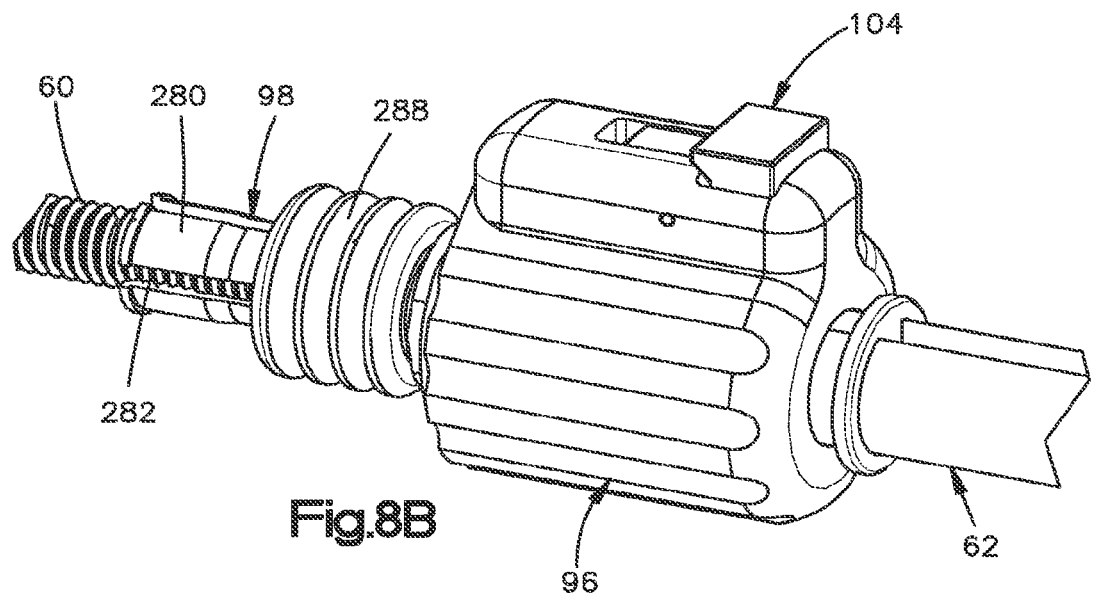

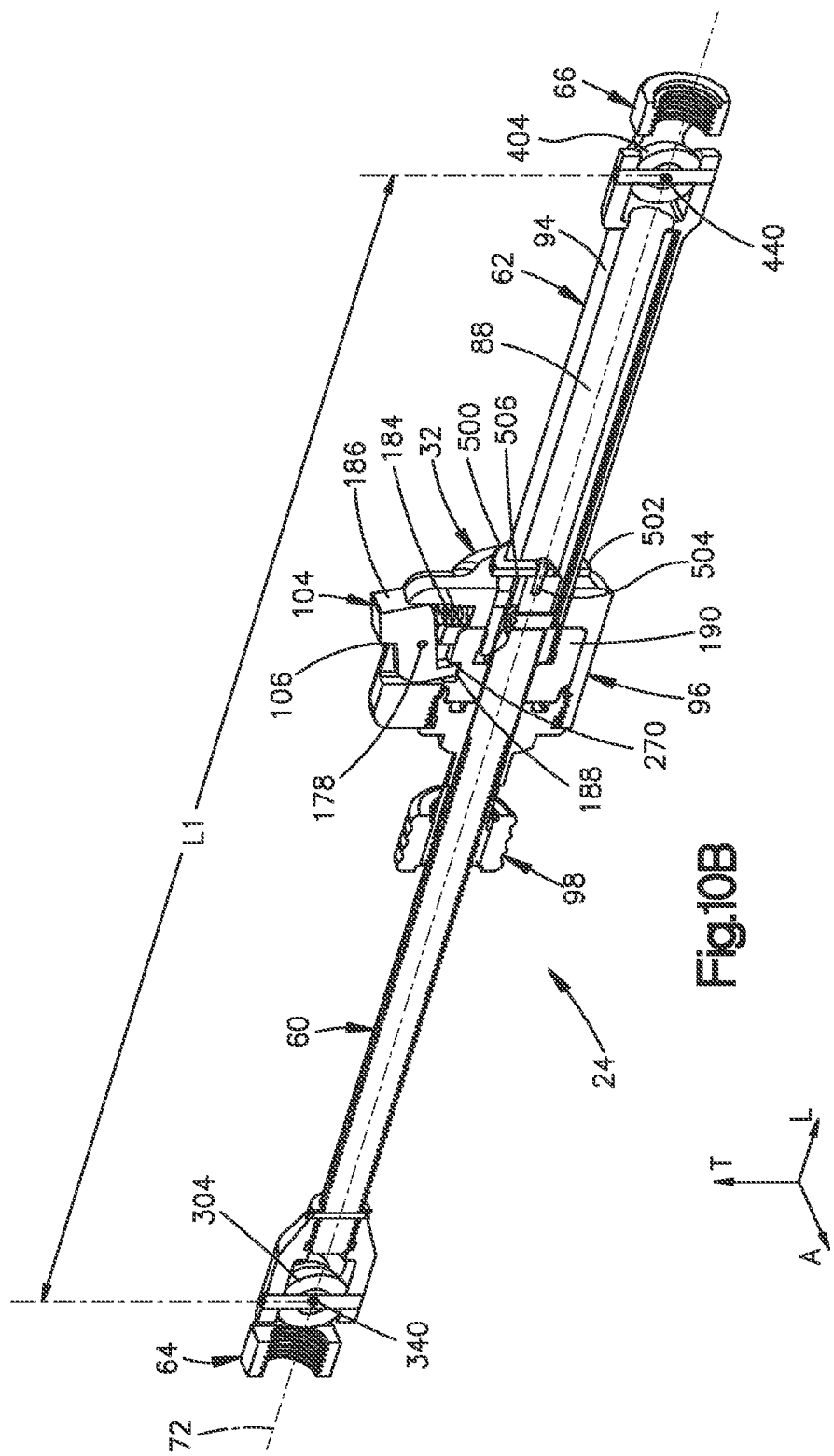

EXTERNAL BONE FIXATION DEVICE

CROSS-REFERENCE TO RELATED APPLICATIONS

This application is a divisional of U.S. application Ser. No. 13/800,319 filed Mar. 13, 2013. U.S. application Ser. No. 13/800,319 is related by subject matter to U.S. application Ser. No. 13/800,545 filed Mar. 13, 2013, which issued Oct. 21, 2014 as U.S. Pat. No. 8,864,763. The above disclosures are hereby incorporated by reference as if set forth in their entireties herein.

TECHNICAL FIELD

The present application relates generally to orthopedics. More specifically, the present application relates to a device and method for the repair of fractures or deformities in long bones.

BACKGROUND

External bone fixation devices are used to stabilize bone segments and to facilitate the healing of bones at a bone repair site. A bone repair site can include a location of a deformity in a bone or an area of injury to a bone. Distraction and reduction/compression devices may be incorporated into an external bone fixation device and may be used to gradually adjust the relative orientation and spacing of portions of the bone on opposite sides of a bone repair site.

An external bone fixation device can include a number of support members configured to be connected to the portions of the bone on opposite sides of the bone repair site, as well as a number of distraction and reduction/compression devices configured to adjust the distance between the support members of the external bone fixation device that are attached to the bone portions on opposite sides of the bone repair site. The distraction devices are configured to move the support members gradually over a determined amount of time. The gradual separation allows new bone to form in the void of the bone repair site. In other cases, reduction or compression across a bone repair site to hold the bone portions together is desired to facilitate healing. Such adjustments, whether distraction or reduction/compression, typically follow a prescribed protocol, or treatment plan. After each adjustment, the distraction and reduction/compression device is typically held fixed for a time allowing the new bone to grow and gain strength. After the bone repair site has healed, the external bone fixation device is removed from the bone portions.

SUMMARY

Various embodiments and methods of an external bone fixation device (and the components of the external bone fixation device) used to stabilize bone segments and to facilitate the healing of bones at a bone repair site are disclosed. In one embodiment, the device includes a strut configured to be connected to a pair of external bone fixation members along a strut axis. The strut includes a strut body having a threaded rod and a sleeve. The threaded rod includes a rod body that is elongate along the strut axis. The rod body defines an outer surface that is at least partially threaded, and the sleeve includes a sleeve body and a bore that extends at least into the sleeve body. The bore is configured to receive at least a portion of the threaded rod such that the threaded rod is translatable relative to the sleeve along the strut axis. The strut further includes an actuator supported by the strut body and threadedly attached to the threaded rod, such that rotation of the actuator relative to the rod about the strut axis translates at least one or both of the rod and the sleeve relative to the other of the rod and the sleeve along the strut axis. The strut further includes a locking mechanism supported by the strut body so as to be pivotal relative to the strut body about a pivot axis between a locked configuration whereby the locking mechanism prevents the actuator from rotating relative to the threaded rod, and an unlocked configuration whereby the locking mechanism does not prevent the actuator from rotating relative to the threaded rod, and the pivot axis is angularly offset with respect to the strut axis.

In another embodiment, a strut configured to be connected to a pair of external bone fixation members along a strut axis includes a strut body having a threaded rod and a sleeve, the threaded rod including a rod body that is elongate along the strut axis, and the rod body defining an outer surface that is at least partially threaded. The sleeve has a sleeve body and a bore that extends at least into the sleeve body, the bore configured to receive at least a portion of the threaded rod such that the threaded rod is translatable relative to the sleeve along the strut axis. The strut further includes an actuator supported by the strut body and threadedly attached to the threaded rod, such that rotation of the actuator relative to the rod about the strut axis translates at least one or both of the rod and the sleeve relative to the other of the rod and the sleeve along the strut axis. The actuator includes a gripping member that is configured to receive a torque that rotates the actuator relative to the threaded rod about the strut axis. The gripping member includes a body and a bore that extends through the body, the body having an inner surface that at least partially defines the bore and an outer surface opposite the inner surface. The bore is configured to at least partially receive the strut body, and the gripping member further includes a projection that is fixed to the gripping member body and extends out from the outer surface of the gripping member body in a direction away from the inner surface of the gripping member body.

In another embodiment, a strut configured to be connected to a pair of external bone fixation members along a strut axis includes a strut body having a threaded rod and a sleeve, the threaded rod including a rod body that is elongate along the strut axis, and defines an outer surface that is at least partially threaded. The sleeve includes a sleeve body and a bore that extends at least into the sleeve body, the bore configured to receive at least a portion of the threaded rod such that the threaded rod is translatable relative to the sleeve along the strut axis. The strut further includes an actuator supported by the strut body and threadedly attached to the threaded rod, such that rotation of the actuator relative to the rod about the strut axis translates at least one or both of the rod and the sleeve relative to the other of the rod and the sleeve along the strut axis. The strut further includes a joint configured to attach to one of the external bone fixation members, the joint including a first hinge body supported by the threaded rod, a second hinge body configured to attach to the external bone fixation member, and a cross coupling member configured to couple the first hinge body to the second hinge body such that first hinge body is rotatable relative to second hinge body about both a first axis that is angularly offset with respect to the strut axis, and a second axis that is angularly offset with respect to both the first axis and the strut axis. Wherein the cross coupling member is substantially spherical.

In another embodiment, a strut configured to be connected to a pair of external bone fixation members along a strut axis includes a strut body having a threaded rod and a sleeve, the threaded rod including a rod body that is elongate along the strut axis and defines an outer surface that is at least partially threaded. The sleeve includes a sleeve body and a bore that extends at least into the sleeve body, and the bore is configured to receive at least a portion of the threaded rod such that the threaded rod is translatable relative to the sleeve along the strut axis. The strut further includes an actuator supported by the strut body and threadedly attached to the threaded rod, such that rotation of the actuator relative to the rod about the strut axis translates at least one or both of the rod and the sleeve relative to the other of the rod and the sleeve along the strut axis. The strut further includes a locking mechanism supported by the strut body so as to be pivotal relative to the strut body about a pivot axis between a locked configuration whereby the locking mechanism prevents the actuator from rotating relative to the threaded rod in response to an applied torque, and an unlocked configuration whereby the locking mechanism does not prevent the actuator from rotating relative to the threaded rod in response to the applied torque. Wherein the locking mechanism includes a lever the lever that defines a first surface, and the strut body defines a second surface that interferes with the first surface so as to prevent rotation of the actuator relative to the threaded rod about the strut axis when the locking mechanism is in the locked configuration, the first and second surfaces oriented such that the first and second surfaces do not cam over one another in response to the applied torque.

In another embodiment, a strut configured to be connected to a pair of external bone fixation members along a strut axis includes a threaded rod having a rod body that is elongate along the strut axis, the rod body defining an outer surface that is at least partially threaded. The strut further has a sleeve including a sleeve body, the sleeve body defining an inner surface that defines a bore that extends at least into the sleeve body and is configured to receive a portion of the rod body. The strut further having an actuator threadedly attached to the threaded rod and rotatably supported by the sleeve. Wherein one of the inner surface and the rod body supports a track that is elongate along a direction parallel to the strut axis, and the other of the inner surface and the rod body fixedly supports a follower configured to ride along the track such that the treaded rod translates with respect to the sleeve along the strut axis when the actuator is rotated with respect to the sleeve and the threaded rod.

In another embodiment, a method of assembling an external bone fixation device configured to repair a deformity in a bone is disclosed. The device includes a strut having a first joint, a second joint, and a length measured from the first joint to the second joint along a strut axis. The first and second joints define first and second fastener receiving holes respectively, and the strut further includes an actuator configured to adjust the length and a locking mechanism configured to be supported by the actuator. The locking mechanism includes a locked configuration in which the actuator is prevented from adjusting the length, and an unlocked configuration in which the actuator is able to adjust the length. The first and second external bone fixation members each include a top surface and a bottom surface. The first and second external fixation members each further including a fastener receiving hole extending from the top surface to the bottom surface, and the first external fixation member defines a center and a radial outward direction that extends from the center to the fastener receiving hole of the first external bone fixation member.

The method includes the step of positioning the strut relative to the first external bone fixation member such that the fastener receiving hole of the first joint is aligned with the fastener receiving hole of the first external fixation member. The method further includes the step of inserting a first fastener into and at least partially through the fastener receiving hole of the first joint and the fastener receiving hole of the first external bone fixation member. The method further includes the step of rotating the actuator about the strut axis such relative to the fastener receiving hole of the first external bone fixation member such that the locking member is spaced from the strut axis in the radial outward direction. The method further includes the step of positioning the strut relative to the second external bone fixation member such that the fastener receiving hole of the second joint is aligned with the fastener receiving hole of the second external fixation member. The method further includes the step of inserting a second fastener into and at least partially through the fastener receiving hole of the second joint and the fastener receiving hole of the second external bone fixation member, such that after the step of inserting of the second fastener through the fastener receiving holes of the second external fixation member and the second joint, the actuator is not rotatable relative to the fastener receiving hole of the first external bone fixation member about the strut axis when the locking mechanism is in the locked configuration.

BRIEF DESCRIPTION OF THE DRAWINGS

The foregoing summary, as well as the following detailed description of illustrative embodiments of the external bone fixation device of the present application, will be better understood when read in conjunction with the appended drawings. For the purposes of illustrating the external bone fixation device of the present application, there is shown in the drawings illustrative embodiments. It should be understood, however, that the application is not limited to the precise arrangements and instrumentalities shown. In the drawings:

FIG. 2A is a perspective view of one of the plurality of bases illustrated in FIG. 1A, according to one embodiment;

FIG. 2B is a top plan view of the base illustrated in FIG. 2A;

FIG. 3 is a perspective view of one of the plurality of bases illustrated in FIG. 1A, according to another embodiment;

FIG. 5B is a top plan view of the strut illustrated in FIG. 5A;

FIG. 5C is a cross-sectional side view of the strut illustrated in FIG. 5B along line 3B-3B;

FIG. 6A is an exploded perspective view of the strut illustrated in FIG. 5;

FIG. 8A is a perspective view of the strut illustrated in FIG. 5A, the strut including a distraction nut, a drive nut, and a clamp in a first position;

FIG. 8B is a perspective view of the actuator illustrated in FIG. 8A, with the clamp in a second position;

FIG. 10B is a cross-sectional view of the strut illustrated in FIG. 10A.

DETAILED DESCRIPTION OF ILLUSTRATIVE EMBODIMENTS

Figure 1A:
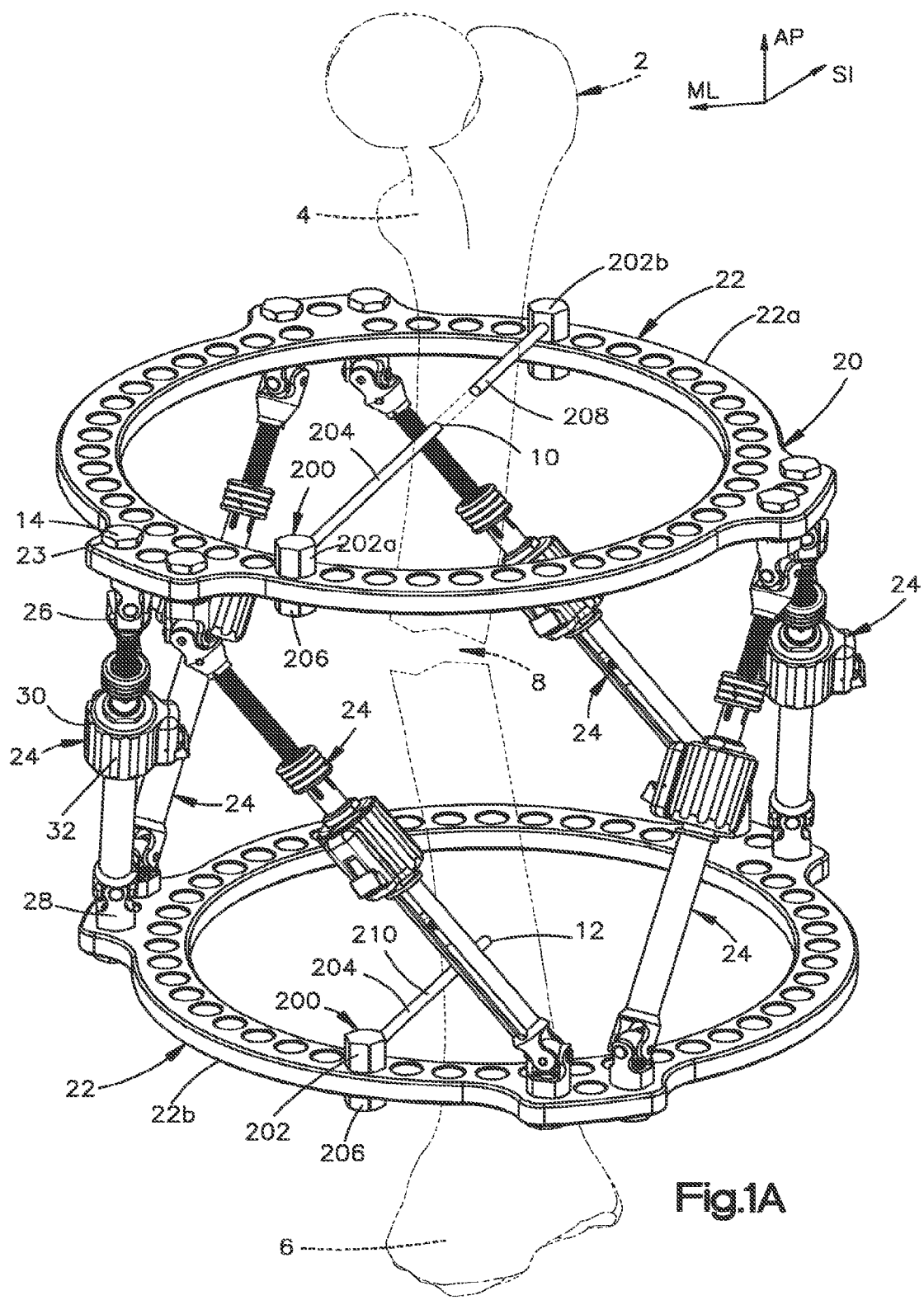
FIG. 1A is a perspective view of an external bone fixation device in a first configuration, positioned proximate a fractured bone, the external bone fixation device including a plurality of bases and a plurality of struts.

Certain terminology is used in the following description for convenience only and is not limiting. The words "right", "left", "lower", "upper", "bottom", and "top" designate directions in the drawings to which reference is made. The words, "anterior", "posterior", "superior", "inferior", "medial", "lateral" and related words and/or phrases designate preferred positions and orientations in the human body to which reference is made. For example, the words "medially" and "laterally" refer to directions toward and away from, respectively, a midline extending vertically through a body. The words "proximal" and "distal" refer to directions toward or away from where an appendage, such as a leg, is joined to the rest of the body, respectively. The terminology includes the above-listed words, derivatives thereof and words of similar import.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. Further, reference to values stated in ranges includes each and every value within that range. All ranges are inclusive and combinable. Certain features of the invention which are described herein in the context of separate embodiments may also be provided in combination in a single embodiment. Conversely, various features of the invention that are described in the context of a single embodiment may also be provided separately or in any subcombination.

A three dimensional coordinate system is used to describe the positions and orientations of the parts of the external bone fixation device. The coordinate system includes a first direction, such as a longitudinal direction L; a second direction, such as a lateral direction A, and a third direction, such as a transverse direction T, wherein each of the directions is perpendicular to both of the other two directions.

Figure 1B:
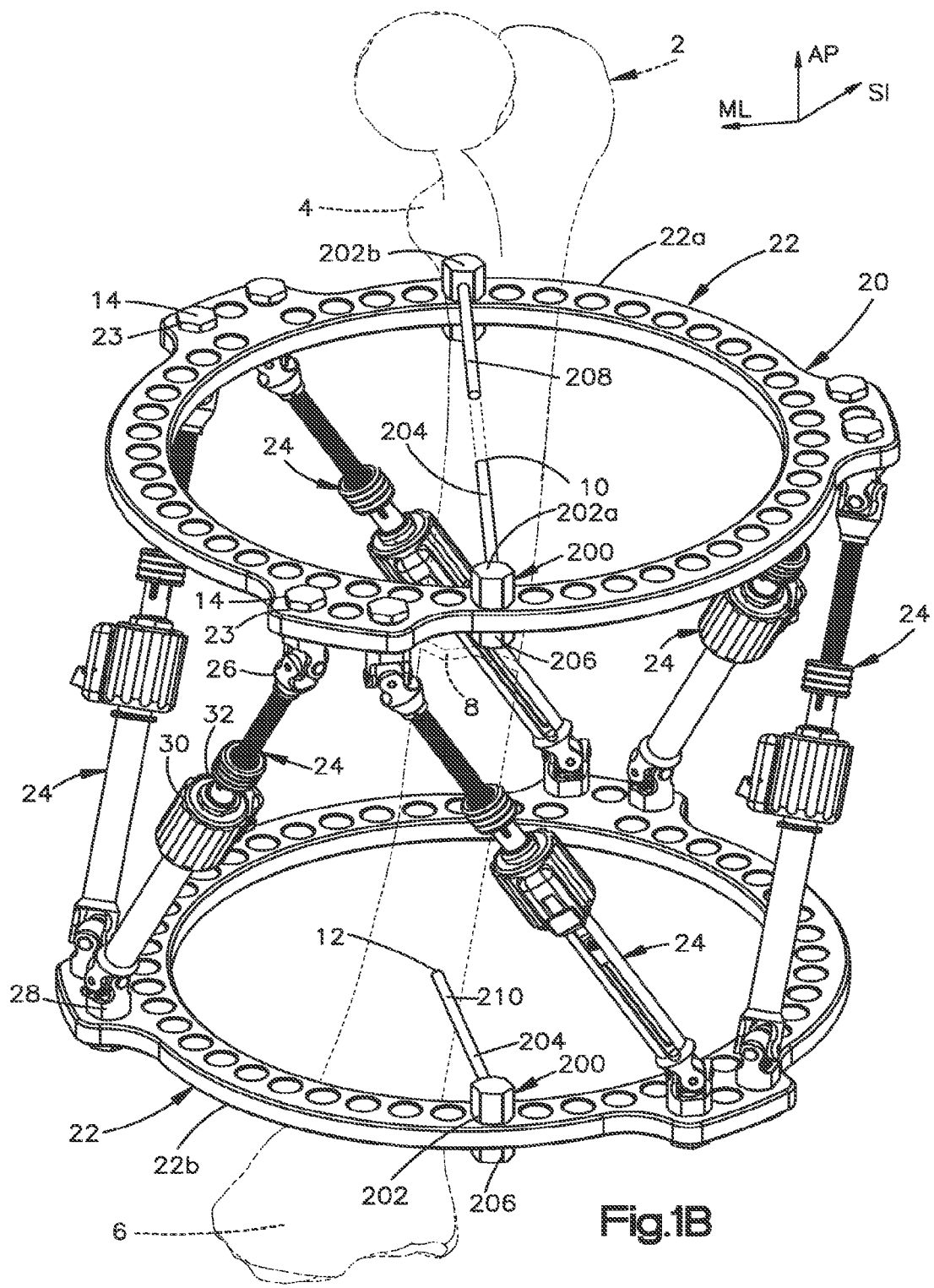
FIG. 1B is a perspective view of the external bone fixation device illustrated in FIG. 1A in a second configuration positioned proximate the fractured bone.

Referring to FIGS. 1A and 1B, an external bone fixation device 20 is configured to be used to correct bone deformities, which can be anatomical deformities or bone injuries such as fractures. In one embodiment the external bone fixation device 20 can be used to treat a fractured long bone 2, such as a femur. The bone 2 can include a first bone portion 4, such as a proximal portion, and a second bone portion 6, such as a distal portion. The first bone portion 4 and the second bone portion 6 can be separated by a defect, such as a fracture 8. The device 20 is configured to attach to the bone 2 at a first location 10 located on the first bone portion 4, and at a second location 12 located on the second bone portion 6. The device 20 is configured to move at least one or both of the first bone portion 4 and the second bone portion 6 relative to the other of the first bone portion 4 or the second bone portion 6, respectively, from a first position, such as a first orientation as shown in FIG. 1A, to a second position that is different from the first position, such as a second orientation different from the first orientation as shown in FIG. 1B, to align the first and second bone portions 4 and 6 so as to assist in correction the bone deformity of the bone 2.

As shown in the illustrated embodiment, the device 20 can include a plurality (e.g., a pair or more) of external bone fixation members, such as bases 22, that are each configured to be secured to respective bone portions, and at least one strut 24, such as a plurality of struts 24, that are configured to attach to at least a pair of the external bone fixation members at attachment locations 23. Fasteners 14, for example bolts or screws, can be used to secure the strut 24 relative to the base 22 at the attachment location 23. The external support members can attach to a bone fixation element 204 that is anchored in the respective bone portion. For instance, the external support member can be supported outboard of the epidermis that surrounds the bone portion, and the bone fixation element 204 can extend from the external support member, through the epidermis and soft tissue disposed between the epidermis and bone portion, and into the bone portion.

For example, the bases 22 can include a first base 22a and a second base 22b. The struts 24 can define respective distraction and reduction/compression devices (collectively referred to herein as "strut" or "struts" 24) configured to attach adjacent ones of the plurality of bases 22 such that the adjacent bases 22 are movable relative to one another. For instance, the struts 24 define a length between the attachment locations 23 that can be adjustable so as to cause at least one of the bases 22 to move relative to the other of the bases 22 at the respective attachment locations 23.

Figure 5A:
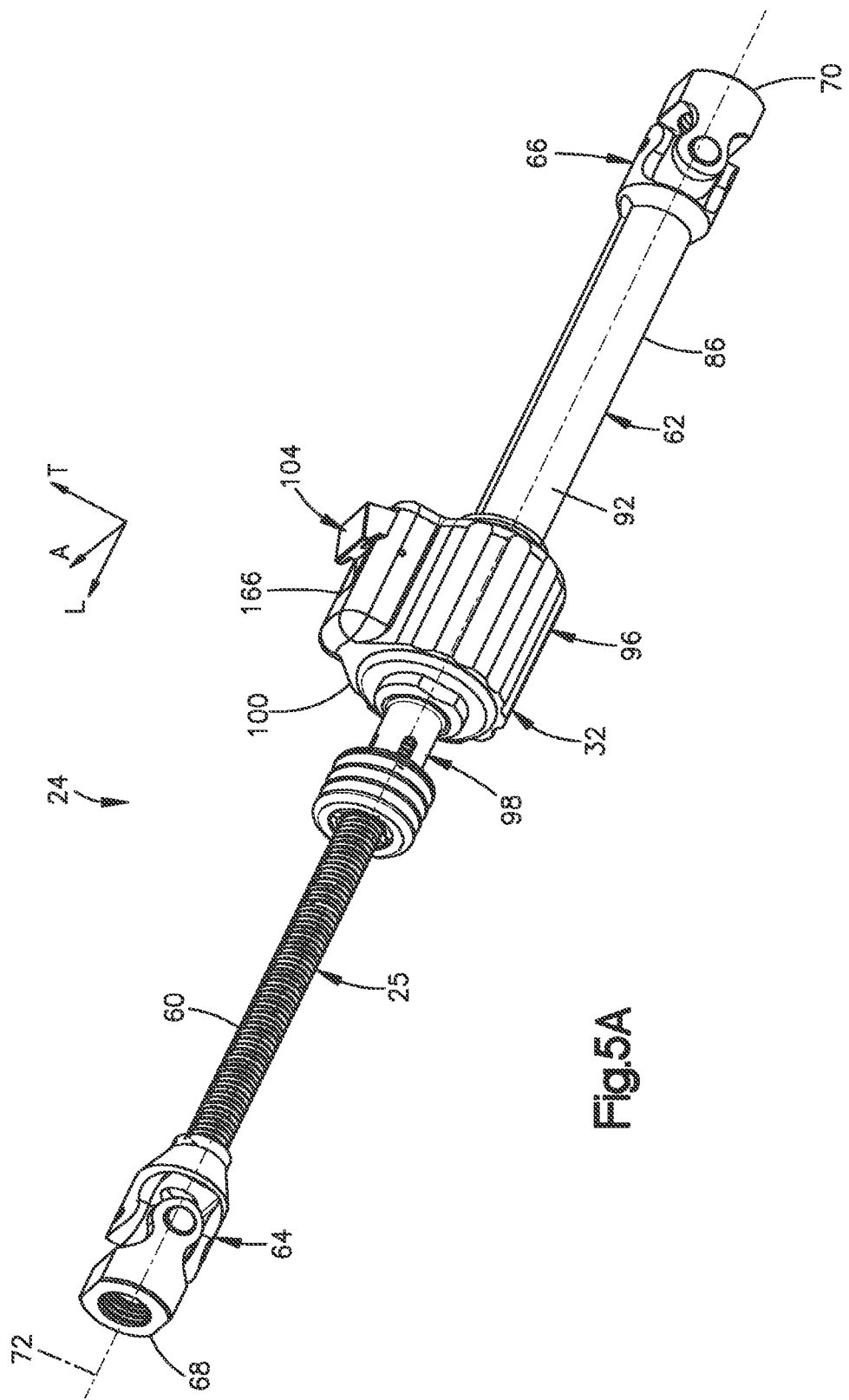
FIG. 5A is a perspective view of one of the plurality of struts illustrated in FIG. 1A, according to one embodiment, the strut including an actuator, a threaded rod, a sleeve, a first joint, and a second joint.

In particular, an increase of the length of the struts 24 can cause one of the attachment locations 23 to move away from the other of the attachment locations, a decrease of the length of the struts 24 can cause one of the attachment locations 23 to move toward the other of the attachment locations 23, and any adjustment of the length (increase or decrease) can cause at least one of the external fixation members to rotate relative to the other of the external fixation members. Each of the struts 24 includes a first end portion 26 configured to be attached to a first of the adjacent bases 22, for example the first base 22a at the attachment location 23, and a second end portion 28 configured to be attached to a second of the adjacent bases 22, for example the second base 22b at the attachment location 23. The struts 24 can further include a strut axis 72 (as shown in FIG. 5A), the strut axis 72 extends from the first end portion 26 to the second end portion 28 such that the strut 24 is elongate along the strut axis 72.

The strut 24 includes an intermediate portion 30 disposed between the first end portion 26 and the second end portion 28. The strut 24 can further include an actuator 32, such that when the actuator 32 is actuated, the first end portion 26 moves relative to the second end portion 28. In one embodiment, the intermediate portion 30 carries or supports the actuator 32, as shown. Actuation, for example rotation, of the actuator 32 of the strut 24 moves the first end portion 26 relative to the second bone portion 28. When the first end portion 26 is attached to the first base 22a and the second end portion 28 is attached to the second base 22b, actuation of the actuator 32 moves the first end portion 26 and the attached first base 22a relative to the second end portion 28 and the attached second base 22b.

The device 20 is configured such that in an assembled configuration, wherein the first end portions 26 and the second end portions 28 of the struts 24 are attached to the first base 22a and the second base 22b, the first base 22a is moveable relative to the second base 22b in up to six degrees of freedom. For example, the first base 22a can translate relative to the second base 22b in either the anterior-posterior direction AP, the medial-lateral direction ML, the superior-inferior direction SI, or any combination thereof. In addition, the first base 22a can rotate relative to the second base 22b about an axis defining the anterior-posterior direction AP, the medial-lateral direction ML, the superior-inferior direction SI, or any combination thereof.

The rotational locking of the strut 24 when attached to one of the bases 22 at both the first and second end portions 26 and 28 may be desired in an application where a certain orientation of the struts 24 relative to the bases 22 is desired. For example, the struts 24 can include visual indications regarding the properties of the strut 24, such as the current length of the strut. The rotational locking of the strut 24 as described above allows a user to have the visual indications facing in a direction that are easily readable by a user when the external bone fixation device 20 is attached to the bone 2.

The device 20, in one embodiment, includes a plurality of attachment mechanisms 200 that are configured to attach the first bone portion 4 to the first base 22a and the second bone portion 6 to the second base 22b such that as the first and second bases 22a and 22b move relative to one another, the first and second bone portions 4 and 6 also move relative to one another. In other words the attachment mechanisms 200 are configured to attach a base 22 to a portion of the bone 2 such that the base 22 and the portion of the bone 2 are translationally and rotationally coupled together.

As shown in the illustrated embodiment, the attachment mechanisms 200 can include a bracket 202 that can be attached to the base 22, for example by a fastener 206. The attachment mechanism 200 further includes the bone fixation element 204 that couples the bracket 202 to the bone 2. The bone fixation element 204 includes, for example, a wire 208 and a rod 210. In one embodiment, the wire 208 is a Kirschner wires (or "K-wire"). As shown, the wire 208 is configured to be attached to a first bracket 202a, extend completely through the bone 2, and be attached to a second bracket 202b on the other side of the bone 2. The rod 210 is configured to be attached to a bracket 202, and extend into, or partially through, the bone 2. As shown, the rod 210 is only attached to one bracket 202. The rod 210 can be threaded or have another retention structure on an end of the rod 210 that is inserted into the bone 2 that aids in securing the rod 210 to the bone 2.

Referring to FIGS. 2A and 2B, the base 22 includes a base body 34. As shown in the illustrated embodiment, the base body 34 can be substantially ring shaped. The base body 34 can be formed from a monolithic piece of material, as shown, or the base body 34 can be formed from separate pieces or segments of material that are joined together. The base 22 can include a base axis 36. In one embodiment, the base axis 36 is a central axis such that the base body 34 is substantially centered about the base axis 36. The base body 34 includes a first surface 38 (or upper surface), a second surface 40 (or lower surface) that is opposite the first surface 38, and a thickness T1 measured from the first surface 38 to the second surface 40. In one embodiment the thickness T1 is constant throughout the base body 34. In another embodiment the thickness T1 is not constant throughout the base body 34.

As shown in the illustrated embodiment, the first surface 38 is substantially planar such that the first surface 38 defines a plane P1. In another embodiment, the second surface 40 is substantially planar such that the second surface 40 defines the plane P1. In another embodiment both the first surface 38 and the second surface 40 are substantially planar such that either the first surface 38 or the second surface 40, or both define the plane P1.

Referring to FIGS. 1A to 2B, the device 20 includes more than one base 22. As shown, the device includes the first base 22a and the second device 22b. The first base 22a and the second base 22b are configured to be attached to the first bone portion 4 and second bone portion 6 of a bone 2, respectively. When the first base 22a and the second base 22b are first attached to the first and second bone portions 4 and 6, the first and second bone portions 4 and 6 are in a first orientation relative to one another. When the first and second bases 22a and 22b are attached to the first and second bone portions 4 and 6 in the first orientation, the first and second bone portions 4 and 6 are in an undesired position such that the planes P1 of the first and second bases 22a and 22b are non-parallel to one another, the base axes 36 of the first and second bases 22a and 22b are non-parallel, or both.

After the first and second bases 22a and 22b are secured to the first and second bone portions 4 and 6 in the first configuration, a treatment plan can be performed to move the first and second bases 22a and 22b into a second orientation. In the second orientation, the first and second bone portions 4 and 6 are in a desired position such that the planes P1 of the first and second bases 22a and 22b are substantially parallel to one another, the base axes 36 of the first and second bases 22a and 22b are substantially parallel, or both. As will be described in detail below, the treatment plan can include actuation of the actuators 32 of the struts 24. In one embodiment the treatment plan includes actuation of the actuators 32 of specified struts 24, a specified amount, over a specified amount of time.

Referring to FIGS. 2A and 2B, the base body 34 further includes a first side wall 44, such as an outer side wall, and an inner side wall 46, such as an inner side wall, that is opposite the first side wall 44. As shown in the illustrated embodiment, the first side wall 44 defines an outer periphery of the base body 34, and the second side wall 46 defines an inner periphery of the base body 34. The base body 34 defines an inner diameter D1 measured from the second side wall 46 at a first location, through the base axis 36, and to the second side wall 46 at a second location. The base body 34 defines an outer diameter D2 measured from the first side wall 44 at a first location, through the base axis 36, and to the first side wall 44 at a second location.

The base 22 can further include an opening 48. The opening 48 is defined by the base body 34, for example the second side wall 46, and the opening 48 is configured to receive the bone 2. The base body 34 defines a width W1 measured from the second side wall 46 to the first side wall 44 in a direction perpendicular to the base axis 36. In one embodiment the width W1 is constant throughout the base body 34. In another embodiment the width W1 is not constant throughout the base body 34.

In one embodiment, the base body 34 includes at least one tab 56. The tab 56 includes a portion of the base body 34 that extends radially outward from the base axis 36 farther than a surrounding portion of the base body 34. As shown, the tab 56 defines a portion of the base body 34 with a greater width W1" than the width W1' of the base body 34 at a location adjacent the tab 56. The base body 34 can include any number of tabs 56 (including no tabs), spaced about the base body 34 in any desired configuration. For example, the base body 34 can include three tabs 56 spaced apart substantially equally about the outer periphery of the base body 34, such that each of the tabs 56 is spaced about 120 degrees from each of the other two tabs 56.

The base 22 also includes a plurality of holes 50. The plurality of holes 50 extend through the base body 34, for example the holes 50 extend though an entirety of the thickness T1 of the base body 34 from the first surface 38 to the second surface 40. The holes 50 are configured to receive the struts 24 and the attachment mechanisms 200. The holes 50 can be threaded, unthreaded, or a combination of threaded and unthreaded such that the holes 50 are configured to receive both locking and non-locking fasteners. In the illustrated embodiment, the holes 50 include a first series holes 50a and a second series of holes 50b. The first series of holes 50a are arranged such that they are positioned on the base body 34 along a first circle 52a. The second series of holes 50b are arranged in the illustrated embodiment, such that they are positioned on a second circle 52b. As shown, the first circle 52a has a smaller diameter than the second circle 52b.

In one embodiment, the second series of holes 50b is positioned along the second circle 52b and the second circle 52b passes through at least one, for example three, tabs 56. The first and second series of holes 50a and 50b can be positioned within the base body 34 such that a first ray line R1 extending from the base axis 36 to the first side wall 44 passes through a hole 50 in the first series of holes 50a and a hole 50 in the second series of holes 50b. The first and second series of holes 50a and 50b can further be positioned within the base body 34 such that a second ray line R2 extending from the base axis 36 to the first side wall 44 passes through a hole 50 in the first series of holes 50a but does not pass through a hole 50 in the second series of holes 50b. The first and second series of holes 50a and 50b can still further be positioned within the base body 34 such that a third ray line R3 extending from the base axis 36 to the first side wall 44 passes through a hole 50 in the second series of holes 50b but does not pass through a hole 50 in the first series of holes 50a.

Each of the holes 50 defines a center 54. The holes 50 are arranged such that adjacent holes 50 define a distance between their centers 54. The distance is referred to hereafter as "chord length C1" for the first series of holes 50a and "chord length C2" for the second series of holes 50b. In one embodiment, the first series of holes 50a are arranged throughout the base body 34 such that the chord length C1' of first adjacent holes 50a' is different from the chord length C1" of second adjacent holes 50a".

Referring to FIG. 3, in another embodiment the device 20 includes a base 122 that defines a base body 134. The base 122 is similar to the base 22 in many aspects such that the description of the base 22 above can be applied to the base 122 except where indicated to the contrary below. As shown, the base body 134 includes a primary base body 135a and a secondary base body 135b. The primary and secondary base bodies 135a and 135b are configured to be connected such that they form a complete ring. In one embodiment the primary base body 135a defines a partial ring, for example about a ⅝ (five-eighths) ring, and the secondary base body 135b defines another partial ring, for example a ⅜ (three/eighths) ring that complements the partial ring of the primary base body 135a such that when the primary and secondary base bodies 135a and 135b are joined, a complete ring is formed.

The use of a base 122 with segments, for example primary and secondary base bodies 135a and 135b provides additional flexibility or options when the device 20 is being assembled and attached to a patient. For example, the primary base body 135a can be placed in a desired position relative to a bone and the secondary base body 135b can be attached to the primary base body 135a in the desired position without having to traverse the base 122 all the way from a distal end of the bone (or appendage) to the desired position.

In another embodiment, the device 20 includes a base 122 that only includes the primary base body 135a such that the base 122 defines only a partial ring shape and a gap. The use of a partial ring shape, for example the primary base body 135a, can allow added flexibility for a patient that the device 20 is attached to. The primary base body 135a can be positioned such that the gap is posterior to (or behind) the patient's knee, allowing the patient's knee to flex without interference from the base body 134.

Figure 4:
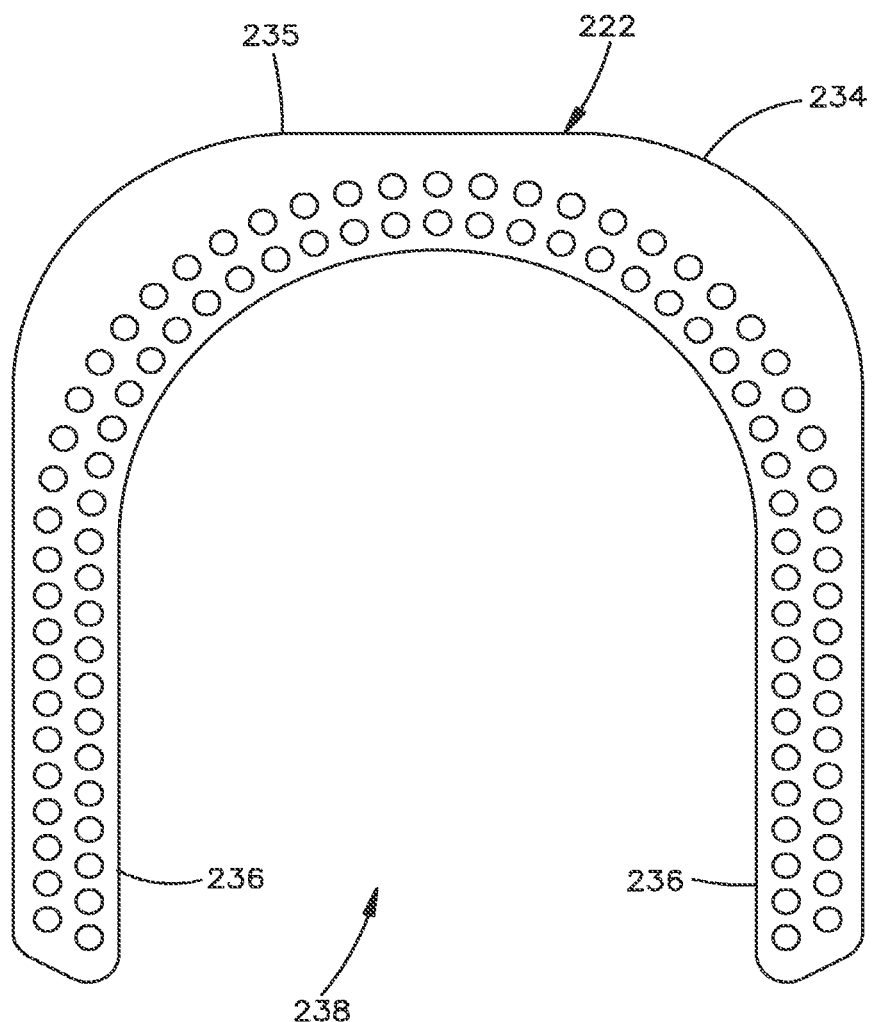
FIG. 4 is a top plan view of one of the plurality of bases illustrated in FIG. 1A, according to another embodiment.

Referring to FIG. 4, in another embodiment the device 20 includes a base 222 that defines a base body 234. The base 222 is similar to the base 22 in many aspects such that the description of the base 22 above can be applied to the base 222 except where indicated to the contrary below. As shown, the base body 234 includes a primary base body 235 and one or more legs 236 extending out from the primary base body 235. As shown, the base body 234 includes two legs 236 extending out from the primary base body 235 such that the legs 236 are substantially parallel to each other. In another embodiment, the legs 236 extend out from the primary base body 235 such that the legs 236 are substantially non-parallel to each other. The base 222 further defines a gap 238 positioned between the legs 236. The base 222 is configured to be placed around an appendage, such as a foot such that the primary base body 235 is positioned posterior to (or behind) a heel of the foot, and the gap 238 is positioned to receive an anterior portion, such as the toes, of the foot. The use of the base 222 in the device 20 allows a patient to walk after the device 20 is attached to the patient, for example during treatment of a deformity or repair of an injury to the patient's foot.

Referring to FIGS. 5A to 5C, in one embodiment, strut 24 includes a strut body 25, the strut body 25 includes, in one embodiment, a first member, for example a threaded rod 60, and a second member, for example a sleeve 62. The threaded rod 60 and the sleeve 62 are configured to be connected such that the threaded rod 60 and the sleeve 62 are translatable relative to one another. The strut 24 further includes a first joint 64 configured to be connected to the threaded rod 60, and a second joint 66 configured to be connected to the sleeve 62. One of the first and second joints 64 and 66, for example the first joint 64, can be a rotatable joint and the other of the first and second joints 64 and 66, for example 66, can be a non-rotatable joint, as described in greater detail below. The strut 24 also includes an actuator 32 configured to be coupled to the strut 24, for example supported by the strut body 25 such that actuation of the actuator 32 translates the threaded rod 60 relative to the sleeve 62.

The strut 24 includes a first end, such as a proximal end 68, and a second end, such as a distal end 70. The strut 24 further includes a strut axis 72 extending from the proximal end 68 to the distal end 70. The strut 24, in one embodiment, is elongate along the strut axis 72. As shown in the illustrated embodiment, the strut axis 72 is a central axis, and the strut axis 72 is parallel to the longitudinal direction L. The strut 24 defines a length L1 measured from a first point 73 to a second point 75 along the strut axis 72. In one embodiment the first point 73 is located at or near the proximal end 68, for example in the first joint 64, and the second point 75 is located at or near the distal end 70, for example in the second joint 66. Actuation of the actuator 32 translates the threaded rod 60 relative to the sleeve 62, changing the length L1.

Referring to FIGS. 5A to 6B, the threaded rod 60 includes a first end, for example a rod proximal end 74, a second end, for example a rod distal end 76, and a rod body 78 that extends from the rod proximal end 74 to the rod distal end 76 and is elongate in the longitudinal direction L, or along the strut axis 72. The rod body 78 includes an outer surface 80 that is at least partially threaded. The threaded rod 60 defines an outer dimension D3, for example an outer diameter. One end of the threaded rod 60, for example the rod proximal end 74, is configured to receive the first joint 64. The strut 24 includes a follower 77. In one embodiment, the follower 77 is supported by the rod distal end 76. The follower 77 is configured to prevent the threaded rod 60 from rotating relative to the sleeve 62 as the threaded rod 60 translates relative to the sleeve 62. The follower 77 can be in the form of a set screw 79 that is configured to be secured to a set screw hole 81 of the threaded rod 60. The set screw 79 includes a head portion 83 and a shaft 85 that extends out from the head portion 83. In one embodiment, the set screw hole 81 is positioned within the rod distal end 76. The rod distal end 76 can include a flat section that is configured to receive the set screw 79 such that the head portion 83 of the set screw 79 abuts the flat section and the shaft 85 of the set screw 79 extends through the set screw hole 81 and protrudes out of the set screw hole 81 and at least partially into a track 89 of the sleeve 62 as described in detail below.

The sleeve 62 includes a first end, for example a sleeve proximal end 82, a second end, for example a sleeve distal end 84, and a sleeve body 86 that extends from the sleeve proximal end 82 to the sleeve distal end 84 and is elongate in the longitudinal direction L. In one embodiment, the sleeve 62 includes a recess, such as a bore 88 that extends into and at least partially through the sleeve body 86 from the sleeve proximal end, in the longitudinal direction towards the sleeve distal end 84. The sleeve body 86, as shown, defines a tube-like structure.

The sleeve body 86 includes a sleeve inner surface 90 that defines the bore 88, and a sleeve outer surface 92 that is opposite the sleeve inner surface 90. The sleeve 62 defines an inner dimension D4, such as an inner diameter measured within the bore 88, and an outer dimension D5, such as an outer diameter. The sleeve outer surface 92 includes an engagement mechanism, for example the sleeve proximal end 82 is at least partially threaded. The sleeve body 86 can be substantially C-shaped such that the sleeve body 86 defines a slot 94. The slot 94 extends in the transverse direction T from the sleeve outer surface 92 to the sleeve inner surface 90, and the slot 94 extends in the longitudinal direction L, or along the strut axis 72, between the sleeve proximal end 82 and the sleeve distal end 84.

The sleeve 62 can further include a track 89 that is configured to receive the follower 77 of the threaded rod 60 such that interference of the follower 77 and the track 89 prevents rotation of the threaded rod 60 relative to the sleeve 62 as the threaded rod 60 translates relative to the sleeve 62. The track 89 extends into the sleeve body 86 from the sleeve inner surface 90 in a direction toward the sleeve outer surface 92. In one embodiment the track 89 does not extend all the way through the sleeve body 86. In another embodiment the track 89 is spaced apart from the slot 94, for example such that if the slot extends through the "top" of the sleeve 62, the track extends towards the "bottom" of the sleeve 62. In another embodiment the track 89 is at least partially aligned with the slot 94.

As shown in the illustrated embodiment, the actuator 32 includes a distraction nut 96, a drive nut 98, and a locking mechanism 104. In one embodiment, the distraction nut 96 and the drive nut 98 are configured to be rotationally and translationally coupled to each other, such that for example, the as the distraction nut 96 translates along the longitudinal direction L, the drive nut 98 also translates along the longitudinal direction L.

The distraction nut 96 includes a gripping member 100, such as an actuator housing 102. In one embodiment, the gripping member 100 carries the locking mechanism 104, for example a lever 106, such that as the gripping member 100 moves (for example translates along the longitudinal direction L or rotates about an axis aligned with the longitudinal direction L) the locking mechanism 104 moves with the gripping member 100. The gripping member 100 is configured to be connected to the sleeve 62 such that the gripping member 100 is rotatable, for example about the longitudinal direction L (or the strut axis 72), relative to the sleeve 62.

The locking mechanism 104 is configured to be connected to, or carried by, the gripping member 100 such that when the locking mechanism is in a first, or locked, configuration the gripping member 100 is rotationally locked with respect to the sleeve 62, preventing the gripping member 100 from rotating relative to the sleeve 62. The locking mechanism is further configured to be connected to or carried by, the gripping member 100 such that when the locking mechanism is in a second, or unlocked configuration the gripping member 100 is rotatable with respect to the sleeve 62.

Referring to FIGS. 5A to 7D, the gripping member 100 includes a proximal end 108, a distal end 110, and a gripping member body 112 extending from the proximal end 108 to the distal end 110. The gripping member body 112 includes an outer surface 114 and an inner surface 116 that is opposite the outer surface 114. The gripping member 100 further includes a bore 118 that is at least partially defined by the inner surface 116. The bore 118 extends into and at least partially through the gripping member body 112 from the proximal end 108 to the distal end 110. As shown in the illustrated embodiment, the bore 118 can include a first portion 160 and a second portion 162.

The gripping member 100 defines a first inner dimension D6 measured within the first portion 160 of the bore 118, and a second inner dimension D7 measured within the second portion 162 of the bore 118. As shown the first and second inner dimensions D6 and D7 can be different, such that the first inner dimension D6 is larger than the second inner dimension D7. The inner surface 116 defining the first portion 160 is partially threaded in one embodiment. In another embodiment, the inner surface defining the first portion 160 is entirely threaded or entirely unthreaded.

The outer surface 114 of the gripping member body 112 is partially cylindrical or a tube-like shape such that the gripping member 100 defines an outer dimension D8, for example an outer diameter, measured from a first point on the outer surface 114, through the strut axis 72, to a second point on the outer surface 114 that is opposite the first point. The gripping member 100 can further include at least one groove 164 that extends into the gripping member body 112 from the outer surface 114 in a direction toward the inner surface 116 such that the groove 164 defines a depth E1. The gripping member 100 can includes multiple grooves 164, as shown, to improve a user's ability to grip and apply a torque to the gripping member 100.

The gripping member 100 can further include a projection 166 that is configured to receive a torque applied to the gripping member 100 to make rotation of the gripping member 100 easier, for example by providing a mechanical advantage. As shown the projection 166 is in the form of a raised portion 168. The raised portion 168 includes at least one projection side wall 170, for example two projection side walls, that extends out from the outer surface 114 of the gripping member body 112 in a direction away from the inner surface 116 of the gripping member body 112. The projection 166 defines a height H1 measured from where the projection side wall 170 extends out from the outer surface 114 and in the direction that the projection side wall extends away from the inner surface 116. In one embodiment, the projection 166 further includes a projection top surface 172 extending between the projection side walls 170.

As shown in the illustrated embodiment, the outer dimension D8 of the gripping member 100 is measured at a location that does not include the projection 166. The gripping member 100 further defines an outer dimension D9 measured from the a first point on the outer surface 114, through the strut axis 72, to a second point located on either the projection side wall 170 or the projection top surface 172. In one embodiment, the projection 166 is configured such that the height H1 of the projection side wall 170 is between about 3 mm and about 9 mm, the outer dimension D8 is between about 15 mm to about 30 mm, and the outer dimension D9 is between about 20 mm and about 35 mm. In another embodiment, the projection 166 is configured such that the height H1 of the projection side wall 170 is about 6 mm, the outer dimension D8 is about 22 mm, and the outer dimension D9 is about 27 mm. In another embodiment, the projection 166 is configured such that the height H1 of the projection side wall 170 is at least 10 percent of the outer dimension D8. In another embodiment, the height H1 of the projection side wall 170 is at least 20 percent of the outer dimension D8. In another embodiment, the height H1 is between about 20 percent and about 30 percent of the outer dimension D8.

In one embodiment, the depth E1 is between about 0.5 mm and about 1 mm. In another embodiment the height H1 is at least 5 times greater than the depth E1. In another embodiment the height H1 is at least 10 times greater than the depth E1. In another embodiment the height H1 is between about 5 and about 10 times greater than E1. For example, in one embodiment, the gripping member 100 can define an outer dimension D8 of about 22 mm, an outer dimension D9 of about 27 mm, a projection height H1 of about 6 mm, and a groove depth E1 of about 0.7 mm.

As shown in the illustrated embodiment, the gripping member 100, specifically the projection 166 carries the locking mechanism 104. The projection 166 includes a projection body 174 and a recess 176 extending into the projection body 174 and terminating at a base surface 177. The recess 176 is configured to at least partially receive the locking mechanism 104. The locking mechanism 104 is configured such that in a first, locked configuration the locking mechanism 104 prevents rotation of the gripping member 100 relative to the sleeve 62. The locking mechanism 104 is further configured such that in a second, unlocked configuration the locking mechanism 104 does not interfere with rotation of the gripping member 100 relative to the sleeve 62.

In one embodiment, the locking mechanism 104 is a lever 106. The lever 106 is configured to be pivotally attached to the gripping member 100. The lever 106 includes a pivot axis 178 that the lever 106 pivots about from the first, locked configuration to the second, unlocked configuration. As shown, locking mechanism 104 can include a pin 182. The lever 106 and the gripping member 100, specifically the projection 166, each include corresponding through holes 180a and 180b, respectively configured to be aligned and receive the pin 182. When the locking mechanism 104 is pivotally attached to the gripping member 100 as described above, the locking mechanism 104 is pivotable from the first, locked configuration to the second, unlocked configuration about an axis, specifically the pivot axis 178, that is non-parallel to the strut axis 72. In another embodiment, the locking mechanism 104 is pivotable from the first, locked configuration to the second, unlocked configuration about an axis, specifically the pivot axis 178, that is substantially perpendicular to the strut axis 72.

As shown in the illustrated embodiment the locking mechanism 104 includes a locking mechanism body 105 and a biasing member, such as a spring 184. The locking mechanism body 105 includes a base portion 186, a stop portion 188, and the pivot axis 178. The base portion 186 can be positioned on one side of the pivot axis 178 and the stop portion 188 can be positioned on the other side of the pivot axis 178 as shown. The recess 176 of the projection 166 is further configured such that when the locking mechanism body 105 is at least partially received within the recess 176 and the locking mechanism body 105 is pivotally attached to the gripping member 100, the spring 184 is configured to be received within the recess 176.

In one embodiment, the spring 184 is configured to be positioned within the recess 176 such that the spring 184 is between the base surface 177 of the projection 166 and the base portion 186 of the locking mechanism body 105. The spring 184 can be configured such that when the locking mechanism body 105 is pivotally attached to the gripping member 100 the spring 184 exerts a biasing force on the base portion 186 of the locking mechanism body 105 in a direction away from the strut axis 72, for example in a direction substantially perpendicular to the strut axis 72, such that the locking mechanism 104 is biased towards the first, locked configuration. In one embodiment, the spring 184 is configured to bias the locking mechanism body 105 into the first, locked configuration even when the strut 24 is under a load, for example during actuation of the actuator 32 to change the length L1 of the strut 24, when the strut 24 is attached to a pair of external bone fixation members, such as the bases 22. Application of a greater force to the base portion 186, in the opposite direction of the biasing force pivots the locking mechanism body 105 about the pivot axis 178 into the second, unlocked configuration.

Referring to FIGS. 5A to 6B, the strut 24 can further include a bearing 190. The bearing 190 is configured to connect the actuator 32 to the sleeve 62 such that the actuator 32 is translationally fixed relative to the sleeve 62, and rotatable about the strut axis 72 relative to the sleeve 62. The bearing includes a proximal end 192, a distal end 194, and a bearing body 196 extending from the proximal end 192 to the distal end 194. The bearing 190 further includes a bearing bore 198 extending into and at least partially through the bearing body 196 from the proximal end 192 to the distal end 194. The bearing, as shown, includes a first portion 260 and a second portion 262.

The bearing 190 defines a first inner dimension D10 measured within the bearing bore 198 at the first portion 260, and a second inner dimension D11 measured within the bearing bore 198 at the second portion 262. As shown the first and second inner dimensions D10 and D11 can be different, such that the first inner dimension D10 is smaller than the second inner dimension D11. The bearing body 196 further includes an inner surface 264 and an outer surface 266 that is opposite the inner surface 264. The inner surface 264 at least partially defines the bearing bore 198. The inner surface 264, for example the second portion 262, is partially threaded in one embodiment. In another embodiment, the inner surface 264 defining the bearing bore 198 within the second portion 262 is entirely threaded or entirely unthreaded.

The bearing 190 further defines a first outer dimension D12 defined by the outer surface 266 measured within the first portion 260, and a second outer dimension D13 defined by the outer surface 266 measured within the second portion 262. As shown the first and second outer dimensions D12 and D13 can be different, for example the first outer dimension D12 can be smaller than the second outer dimension D13.

The strut 24 can further include a locking feature 268, for example a recess 270 configured to receive the stop portion 188 of the locking mechanism 104. In one embodiment the recess 270 is defined by the bearing 190. The recess 270 and the stop portion 188, in one embodiment, have corresponding shapes such that when the locking mechanism 104 is in the first, locked configuration the stop portion 188 is at least partially received within the recess 270 preventing any rotation of the locking mechanism 104 relative to the bearing 190. When the locking mechanism 104 is in the second, unlocked configuration the stop portion 188 is completely removed from the recess 270 such that the locking mechanism 104 can rotate relative to the bearing 190, for example about the strut axis 72.

Referring to FIGS. 5A to 6B, 8A and 8B, the actuator 32 can further include a drive nut 98 that is rotationally and translatably locked relative to the distraction nut 96. The drive nut 98 is further configured to engage the threaded rod 60 such that the drive nut 98 is rotatable and translatable relative to the threaded rod 60. As shown in the illustrated embodiment, the drive nut 98 includes an attachment portion 272, a collet portion 274, and an intermediate portion 276 between the attachment portion 272 and the collet portion 274. The attachment portion 272 is configured to be secured to the distraction nut 96. For example, the attachment portion 272 can include an outer surface 278 that is at least partially threaded. The threaded outer surface 278 of the attachment portion 272 is configured to engage the threaded inner surface 116 of the distraction nut 96. When the corresponding threaded inner surface 116 and threaded outer surface 278 are engaged, the distraction nut 96 and the drive nut 98 are secured relative to one another both translationally and rotationally.

The collet portion 274 of the drive nut 98 is configured to releasably engage with the threaded rod 60 both rotationally and translatably. As shown, the collet portion 274 includes a plurality of flexible fingers 280, each flexible finger 280 being separated from an adjacent flexible finger 280 by a gap 282. Each of the flexible fingers 280 includes an inner surface 284 and an outer surface 286 opposite the inner surface 284. The inner surface 284 of the flexible fingers 280 is at least partially threaded such that the threaded inner surface 284 of the collet portion 274 corresponds to the threaded outer surface 80 of the threaded rod 60.

The collet portion 274 includes an open configuration in which the threaded inner surface 284 is capable of translating relative to the threaded rod 60 without rotating the drive nut 98 relative to the threaded rod 60. In the open configuration, a user is able to make quick, relatively large adjustments to the length L1 of the strut 24 by simply translating the threaded rod 60 relative to the sleeve 62 without the need to rotate or actuate the actuator 32. The collet portion 274 further includes a closed configuration in which the threaded inner surface 284 engages the threaded rod 60 such that the drive nut 98 cannot translate relative to the threaded rod 60 without rotating the drive nut 98 relative to the threaded rod 60.

The drive nut 98 can further include a clamp 288, for instance a ring clamp 290 as shown in the illustrated embodiment. The clamp 288 includes a clamp body 292 and a through hole 294 passing through the clamp body 292. The clamp body 292 includes an inner surface 296 that at least partially defines the through hole 294. The clamp body 292 further defines an inner dimension D14, for example an inner diameter, that is configured such that the clamp 288 is configured to be slidably attached to the intermediate portion 276 and the collet portion 274. As shown, the intermediate portion 276 or the collet portion 274 is configured to pass at least partially through the through hole 294.

Referring to FIGS. 8A and 8B, the clamp 288 is moveable relative to the drive nut 98 between a first position (as shown in FIG. 8A) and a second position (as shown in FIG. 8B), such that in the first position the collet portion 274 passes at least partially though the through hole 294. In the first position the clamp 288 biases or compresses the flexible fingers 280 of the collet portion 274 into the closed configuration. In the second position the intermediate portion 276 passes at least partially through the through hole 294 such that the clamp 288 does not bias the flexible fingers 280 of the collet portion 274 into the closed configuration. In one embodiment, the flexible fingers 280 of the collet portion 274 are naturally biased into the open configuration, such that if the clamp 288 is in the second position, and thus not biasing the flexible fingers 280 into the closed configuration, the collet portion 274 will be in the open configuration allowing the drive nut 98 to translate freely along the threaded rod 60 without rotating the drive nut 98 relative to the threaded rod 60.

In one embodiment, the actuator 32 can be made of a radiolucent material such as a polymer, for example polyether ether ketone (PEEK). Use of a radiolucent material such as PEEK in one or more portions of the strut 24 provides a clear radiography image of the bone 2 and other parts of the device 20 made from radiopaque materials, which may assist the development a treatment plan for the external bone fixation device 20 to correct a bone defect or repair a bone injury. In another embodiment, any combination of the threaded rod 60, sleeve 62, actuator 32, first joint 64, and second joint 66, either in whole or in part is formed from a radiolucent material such as PEEK. In another embodiment, any one of or any combination of the threaded rod 60, sleeve 62, actuator 32, first joint 64, and second joint 66, either whole or in part, is formed from a polyetherimide (PEI), for example Ultem. In another embodiment, any one of or any combination of the threaded rod 60, sleeve 62, actuator 32, first joint 64, and second joint 66, either whole or in part, is formed from a polyoxymethylene (POM), for example Delrin. In another embodiment, any one of or any combination of the threaded rod 60, sleeve 62, actuator 32, first joint 64, and second joint 66, either whole or in part, is formed from a polyphenylsulfone (PPSF or PPSU), for example Radel. In one embodiment, the locking mechanism 104 can be formed, either in whole or in part, from titanium, titanium alloy, aluminum, or aluminum alloy.

Referring to FIGS. 5A to 6B, the strut 24 further includes the first joint 64 and the second joint 66. The first joint 64 is described below as a non-rotatable joint attached to the threaded rod 60 and the second joint 66 is described as a rotatable joint (that includes a shoulder 452) attached to the sleeve 62. It should be understood that in one embodiment, the first (non-rotatable) joint 64 can be attached to the sleeve 62 and the second (rotatable) joint 66 can be attached to the threaded rod 60. In another embodiment, the strut 24 can include two first (non-rotatable) joints 64, one attached to the threaded rod 60 and one attached to the sleeve 62. In another embodiment, the strut 24 can include two second (rotatable) joints 66, one attached to the threaded rod 60 and one attached to the sleeve 62.

The first joint 64 is configured to be located at one of the first end and the second end, for example the proximal end 68, of the strut 24 and the second joint 66 is configured to be located at the other of the first end and the second end, for example the distal end 70, of the strut 24. The first and second joints 64 and 66 are configured to attach the strut 24 to the first and second bases 22a and 22b. The first joint 64 includes a first hinge body 300, a second hinge body 302, and a cross coupling member 304 that is configured to pivotally connect the first and second hinge bodies 300 and 302. In one embodiment, the first joint 64 includes a fastener receiving hole 350 that extends into and at least partially through the second hinge body 302. The fastener receiving hole 350 is configured to receive a fastener 14 (as shown in FIG. 1A) that is inserted through the fastener receiving hole 50 of the base 22 and into the fastener receiving hole 350 of the first joint 64 to attach the strut 24 to the base 22 at the attachment location 23. The term "non-rotatable joint" used herein refers to a joint, for example the first joint 64, that is configured such that when the non-rotatable joint is attached to the base 22, for example by a fastener 14 as described above, the second hinge body 302 does not rotate relative to the base 22.

The first joint 64, in one embodiment, is configured as a universal joint such that the first and second hinge bodies 300 and 302 are rotationally coupled about a first axis, and rotatable relative to one another about a second axis and a third axis. For example, the first and second hinge bodies 300 and 302 are configured to be rotationally coupled about the strut axis 72 and pivotal relative to one another about a first pivot axis 306 and a second pivot axis 308. In the illustrated embodiment, the first and second pivot axes 306 and 308 define a plane that is perpendicular to the strut axis 72. The first and second hinge bodies 300 and 302 are rotatable relative to each other about any axis that lies in the plane.

The first hinge body 300 includes a base portion 310 and a pair of legs 312, extending out from the base portion 310. The legs 312 are spaced apart from one another to define a first gap 314 that is configured to at least partially receive the cross coupling member 304. The second hinge body 302 includes a base portion 316 and a pair of legs 318, extending out from the base portion 316. The base portion 316 includes a base surface 354 configured to face the base 22 when the first joint 64 is attached to the base 22. The second hinge body 302 includes a fastener receiving hole 350 extending into the base portion 316. The second hinge body 302 can include threads 356 such that the fastener receiving hole 350 is threaded. In one embodiment, fastener receiving hole 350 is threaded along its entire length, such that the threads 356 abut the base surface 354 with no gap between the threads 356 in the fastener receiving hole 350 and the base surface 354. The legs 318 are spaced apart from one another to define a second gap 320 that is configured to at least partially receive the cross coupling member 304.

The pair of legs 312 and 318 of both the first and second hinge bodies 300 and 302 can further include an attachment feature configured to secure the cross coupling member 304 within the first and second gaps 314 and 320. As shown, the pair of legs 312 of the first hinge body 300 includes a first pin hole 322 configured to receive a first pin 324, and the pair of legs 318 of the second hinge body 302 includes a second pin hole 326 configured to receive a second pin 328.

The cross coupling member 304 includes a body 330 that is configured to be at least partially received between the first and second gaps 314 and 320. In one embodiment, the body 330 is substantially spherical. In another embodiment the cross coupling member 304 is made from a first material and the first and second hinge bodies 300 and 302 are made from second material that is different from the first material. The first material can be more radiopaque than the second material. For example, the cross coupling member 304 can be made from titanium and the first and second hinge bodies 300 and 302 can be made from aluminum. The shape of the substantially spherical body 330 and the difference in materials between the cross coupling member 304 and the first and second hinge bodies 300 and 302 can improve the use of radiography, such as x-rays, to plan a treatment plan using the external bone fixation device 20 to correct a bone defect or repair a bone injury. For example, the substantially spherical body 330 will appear as a circle (or substantially as a circle) in an x-ray taken from any angle about the external bone fixation device. Forming the cross coupling member 304 from a more radiopaque material than the first and second hinge bodies 300 and 302 will result in the cross coupling member appearing brighter on the x-ray than the surrounding structure.

The cross coupling member 304 further includes a first pin hole 332, the first pin 324, a second pin hole 334, and the second pin 328. The first pin hole 332 of the cross coupling member 304 is configured to receive the first pin 324 when the first pin hole 332 is aligned with the first pin hole 322 of the first hinge body 300. The second pin hole 334 of the cross coupling member 304 is configured to receive the second pin 328 when the second pin hole 334 is aligned with the second pin hole 326 of the second hinge body 302. As shown the first and second pin holes 332 and 334 of the cross coupling member 304 pass through one another, for example at about a 90 degree angle. One of the first and second pin holes 332 and 334 can be larger than the other of the first and second pin holes 332 and 334, such that the larger of the pin holes 332 and 334 is configured to receive a larger one of the first and second pins 324 and 328. For example, the second pin hole 334 and the second pin 328 can be larger than the first pin hole 332 and the first pin 324. The second pin hole 334 can include a cross hole 336 that is configured to be aligned with the first pin hole 332 and receive the first pin 324.

The first hinge body 300 is configured to be coupled to the threaded rod 60, such that the threaded rod 60 and the first hinge body 300 are translationally and pivotally coupled to each other. In one embodiment, the base portion 310 of the first hinge body 300 includes a recess 338 that is configured to at least partially receive the rod proximal end 74 of the threaded rod 60, and a pin 342. The rod body 78 and the base portion 310 can include matching pin holes 341a and 341b configured to be aligned and then receive the pin 342. Once the pin 342 is inserted through the aligned matching pin holes 341a and 341b, the threaded rod 60 and the first joint 64 are translationally and rotationally coupled with respect to one another. Although the first hinge body 300 and the threaded rod 60 are shown as separate parts that are releasable and coupleable to each other, in another embodiment, the first hinge body 300 and the threaded rod 60 can be formed from a single piece of material, or monolithically formed.

The second joint 66 includes a first hinge body 400, a second hinge body 402, and a cross coupling member 404 that is configured to pivotally connect the first and second hinge bodies 400 and 402. In one embodiment, the second joint 66 includes a fastener receiving hole 450 that extends into and at least partially through the second hinge body 402. The fastener receiving hole 450 is configured to receive a fastener 14 (as shown in FIG. 1A) that is inserted through the fastener receiving hole 50 of the base 22 and into the fastener receiving hole 450 of the second joint 66 to attach the strut 24 to the base 22 at the attachment location 23. The term "rotatable joint" used herein refers to a joint, for example the second joint 66, that is configured such that when the rotatable joint is attached to the base 22, for example by a fastener 14 as described above, the second hinge body 402 is rotatable relative to the base 22.

The second joint 66, as shown in the illustrated embodiment, is configured as a universal joint such that the first and second hinge bodies 400 and 402 are rotationally coupled about a first axis, and rotatable relative to one another about a second axis and a third axis. For example, the first and second hinge bodies 400 and 402 are configured to be rotationally coupled about the strut axis 72 and pivotable relative to one another about a first pivot axis 406 and a second pivot axis 408. In the illustrated embodiment, the first and second pivot axes 406 and 408 define a plane that is perpendicular to the strut axis 72. The first and second hinge bodies 400 and 402 are rotatable relative to each other about any axis that lies in the plane defined by the first and second pivot axes 406 and 408.

The first hinge body 400 includes a base portion 410 and a pair of legs 412, extending out from the base portion 410. The legs 412 are spaced apart from one another to define a first gap 414 that is configured to at least partially receive the cross coupling member 404. The second hinge body 402 includes a base portion 416 and a pair of legs 418, extending out from the base portion 416. The base portion 416 includes a base surface 454 configured to face the base 22 when the second joint 66 is attached to the base 22. The second hinge body 402 includes a fastener receiving hole 450 extending into the base portion 416 from the base 454 in a direction toward the pair of legs 418 such that the fastener receiving hole 450 defines a length. The second hinge body 402 can further include threads 456 such that the fastener receiving hole 450 is threaded. In one embodiment, fastener receiving hole 450 is threaded along a portion of its length, such that the threads 456 do not abut the base surface 454. Instead a shoulder 452 (for example in the form of a gap or unthreaded portion) is positioned between the threads 456 in the fastener receiving hole 450 and the base surface 454. The shoulder 452 is configured such that when the second hinge 66 is attached to the base 22, the second hinge 66 is rotatable relative to the base 22. The legs 418 are spaced apart from one another to define a second gap 420 that is configured to at least partially receive the cross coupling member 404.

The pair of legs 412 and 418 of both the first and second hinge bodies 400 and 402 can further include an attachment feature configured to secure the cross coupling member 404 within the first and second gaps 414 and 420. As shown, the pair of legs 412 of the first hinge body 400 includes a first pin hole 422 configured to receive a first pin 424, and the pair of legs 418 of the second hinge body 402 includes a second pin hole 426 configured to receive a second pin 428.

Similarly to the cross coupling member 304 of the first joint 64 described above, the cross coupling member 404 of the second joint 66, in one embodiment, includes a body 430 that is configured to be at least partially received between the first and second gaps 414 and 420. The body 430, as shown, is substantially spherical and can be made from a first material, for example titanium, and the first and second hinge bodies 400 and 402 can be made from second material, for example aluminum, that is different from the first material. The shape of the substantially spherical body 430 and the choice of materials for the cross coupling member and the first and second hinge bodies 400 and 402 can be selected to improve the use of radiography, such as x-rays, to plan a treatment plan using the external bone fixation device 20 to correct a bone defect or repair a bone injury.

The cross coupling member 404 further includes a first pin hole 432, the first pin 424, a second pin hole 434, and the second pin 428. The first pin hole 432 of the cross coupling member 404 is configured to receive the first pin 424 when the first pin hole 432 is aligned with the first pin hole 422 of the first hinge body 400. The second pin hole 434 of the cross coupling member 404 is configured to receive the second pin 428 when the second pin hole 434 is aligned with the second pin hole 426 of the second hinge body 402. As shown the first and second pin holes 432 and 434 of the cross coupling member 404 pass through one another, for example at about a 90 degree angle. One of the first and second pin holes 432 and 434 can be larger than the other of the first and second pin holes 432 and 434, such that the larger of the pin holes 432 and 434 is configured to receive a larger one of the first and second pins 424 and 428. For example, the second pin hole 434 and the second pin 428 can be larger than the first pin hole 432 and the first pin 424. The second pin hole 434 can include a cross hole 436 that is configured to be aligned with the first pin hole 432 and receive the first pin 424.

The first hinge body 400 is configured to be coupled to the sleeve 62, such that the sleeve 62 and the first hinge body 400 are translationally and pivotally coupled to each other. As shown in the illustrated embodiment, the base portion 410 of the first hinge body 400 is integral with the sleeve 62 such that the first hinge body 400 and the sleeve 62 are monolithic. In another embodiment the base portion 410 includes a recess configured to at least partially receive the sleeve 62. In another embodiment, the base portion 410 includes a post configured to be at least partially received within the bore 88 of the sleeve. In another embodiment, the sleeve 62 and the base portion 410 can include matching pin holes configured to be aligned and then receive a pin as described in detail above in reference to the first joint 64.

Figure 6B:
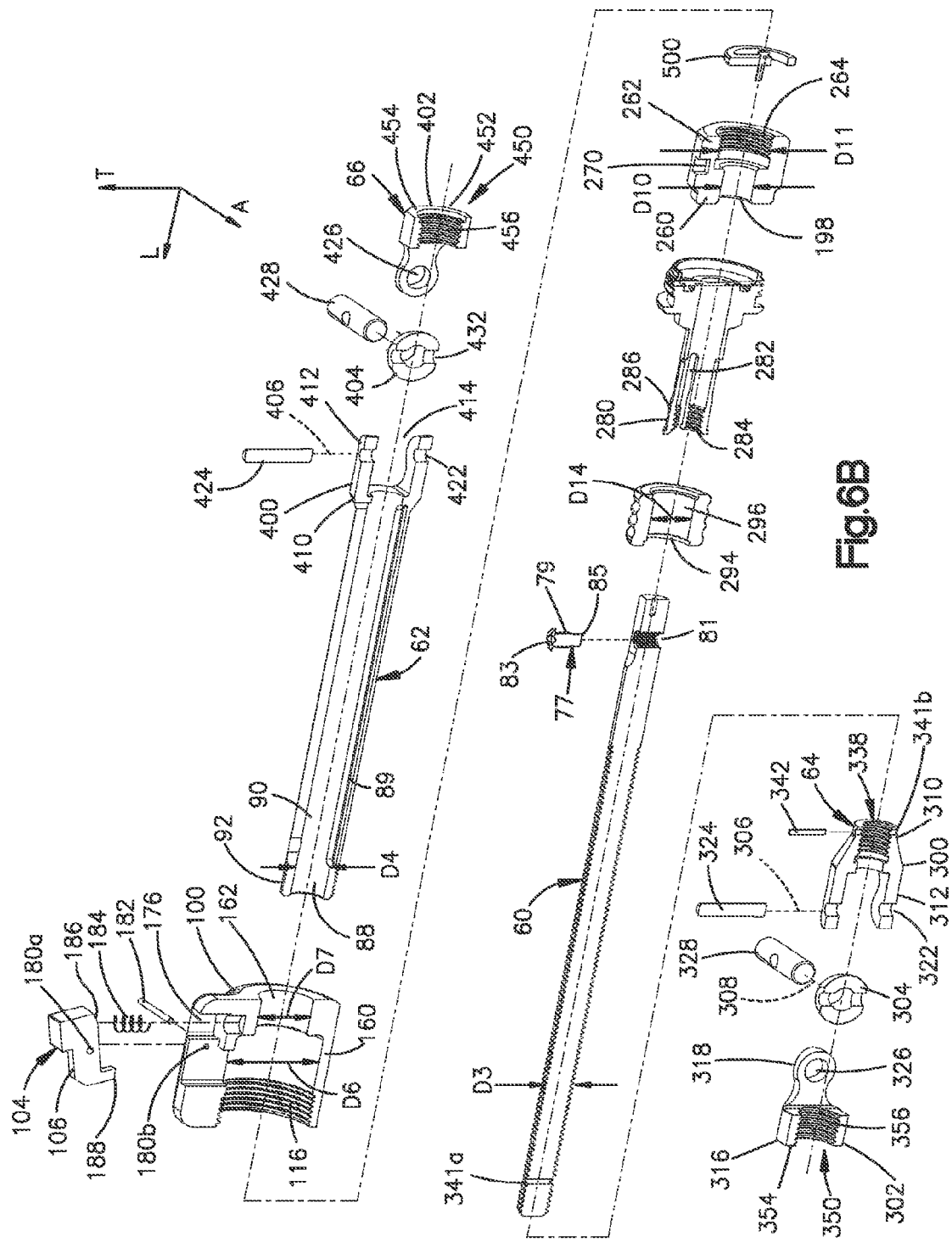
FIG. 6B is an exploded, cross-sectional view of the strut illustrated in FIG. 7A.
Figure 7A:
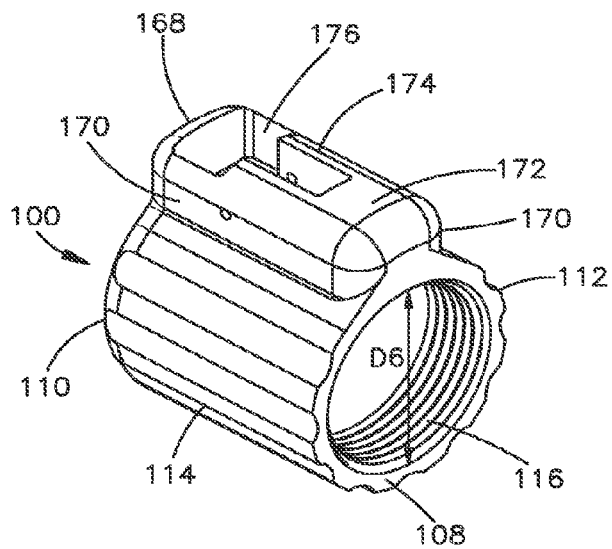
FIG. 7A is a perspective view of a gripping member of the actuator illustrated in FIG. 5A.
Figure 7C:
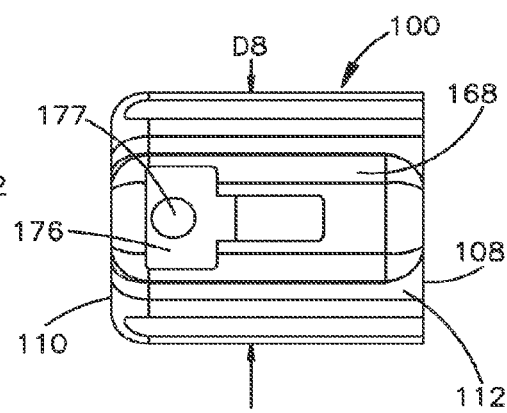
FIG. 7C is a top plan view of the gripping member illustrated in FIG. 7A.
Figure 7B:
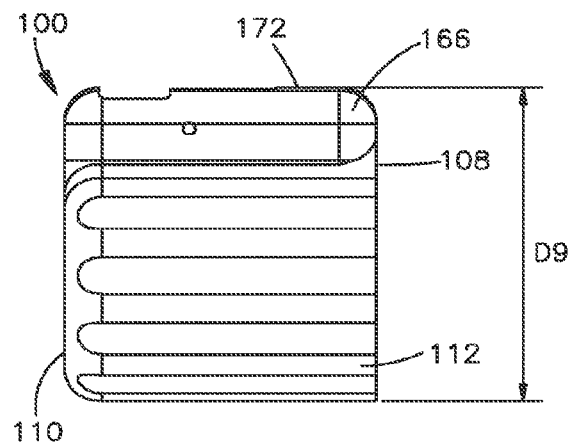
FIG. 7B is a side elevation view of the gripping member illustrated in FIG. 7A.
Figure 7D:
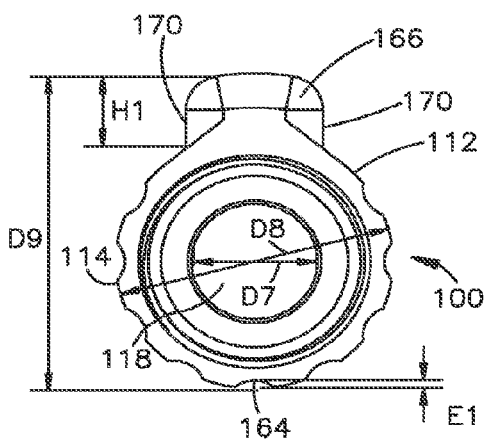
FIG. 7D is a front elevation view of the gripping member illustrated in FIG. 7A.

Referring to FIGS. 6A and 6B, in one embodiment the strut 24 can be assembled as described below. The threaded rod 60 is inserted into the bore 88 of the sleeve 62 such that the follower 77 is at least partially received within the track 89. Once the threaded rod 60 is positioned within the sleeve 62 as described, the threaded rod 60 and the sleeve 62 are translatable relative to each other along the strut axis 72, but they are not rotatable relative to each other about the strut axis 72. The bearing 190 is attached to the sleeve outer surface 92 such that the bearing 190 and the sleeve 62 are rotationally and translationally coupled relative to one another. For example the threaded inner surface 264 of the bearing can be threadedly engaged with the threaded sleeve outer surface 92. The threaded rod 60 passes through the bearing bore 198 such that the threaded rod 60 is translatable relative to the bearing 190.

The actuator 32 is attachable to the strut 24 such that the bearing 190 is at least partially received within the bore 118 of the distraction nut 96 such that the bearing 190 is rotatable relative to the distraction nut 96 about the strut axis 72. The drive nut 98 is attachable to the distraction nut 96 such that the drive nut 98 and the distraction nut are translationally and rotationally coupled to each other. When the drive nut 98 and the distraction nut 96 are attached as described above, the bearing 190 is positioned within the first portion 160 of the bore 118 of the distraction nut 96, such that the bearing is translationally secured relative to the actuator 32 along the strut axis 72 and rotatable about the strut axis 72 relative to the actuator 32.

The drive nut 98 is configured to be placed in the closed configuration by moving the clamp 288 into the first position such that the collet portion 274 is compressed and threaded inner surface 284 of the flexible fingers 280 threadedly engages the threaded outer surface 80 of the threaded rod 60. In the closed configuration rotation of the drive nut 98 relative to the threaded rod 60 about the strut axis 72 translates the drive nut 98 relative to the threaded rod 60 along the strut axis 72. The clamp 288 can be moved into the second position placing the drive nut 98 in the open configuration such that the threaded inner surface 284 of the flexible fingers 280 does not threadedly engage the threaded outer surface 80 of the threaded rod 60. In the open configuration the drive nut 98 is translatable relative to the threaded rod 60 along the strut axis 72 without rotating the drive nut 98 relative to the threaded rod 60 about the strut axis 72.

The first joint 64 is attachable to the rod proximal end 74 such that the first hinge body 300 is both translationally (along the strut axis 72) and rotatably (about the strut axis 72) coupled to the threaded rod 60. The second joint 66 is attachable to the sleeve distal end 84 such that the first hinge body 400 is both translationally (along the strut axis 72) and rotatably (about the strut axis 72) coupled to the sleeve 62.

Figure 9A:
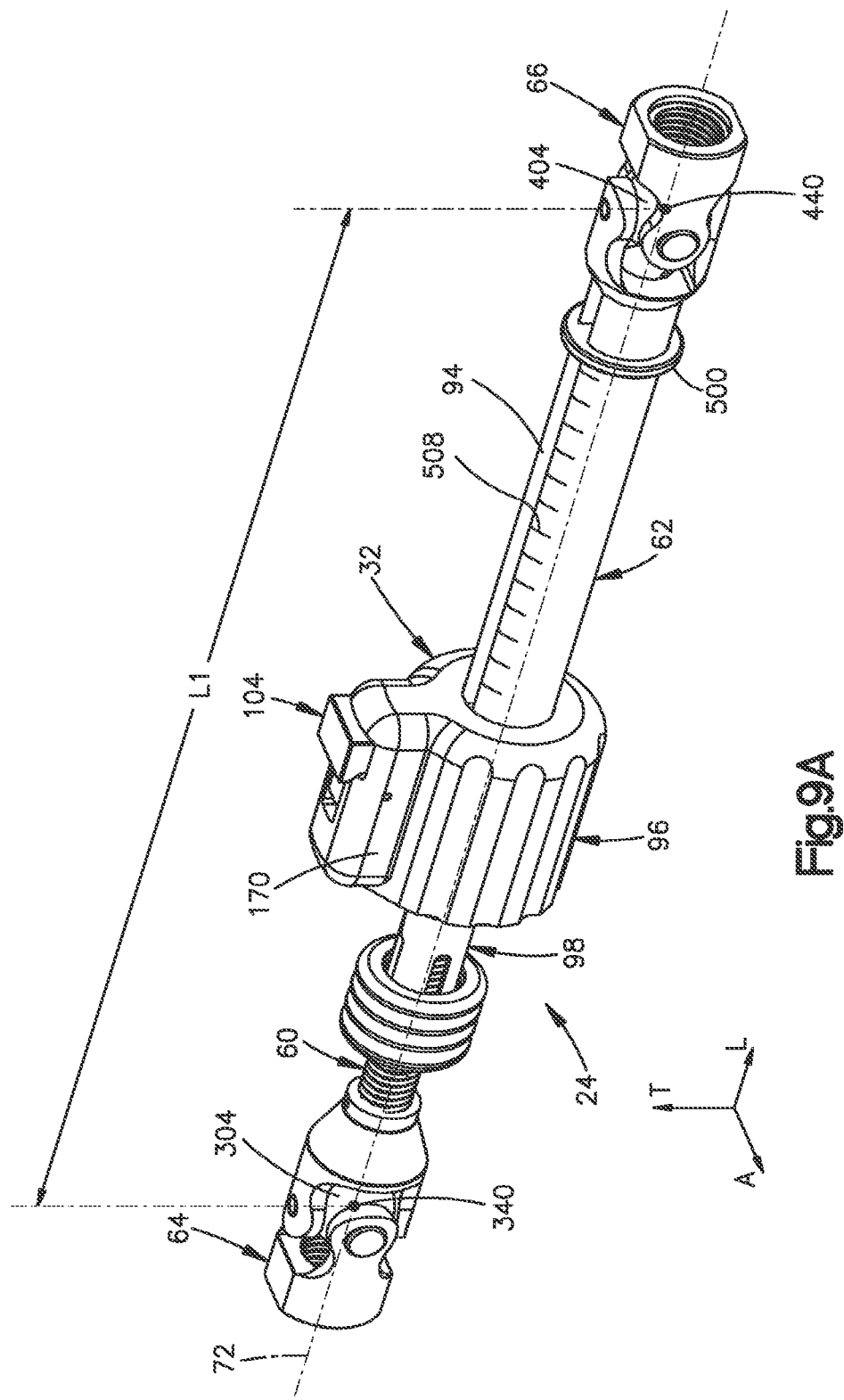
FIG. 9A is a perspective view of the actuator illustrated in FIG. 5A.
Figure 9B:
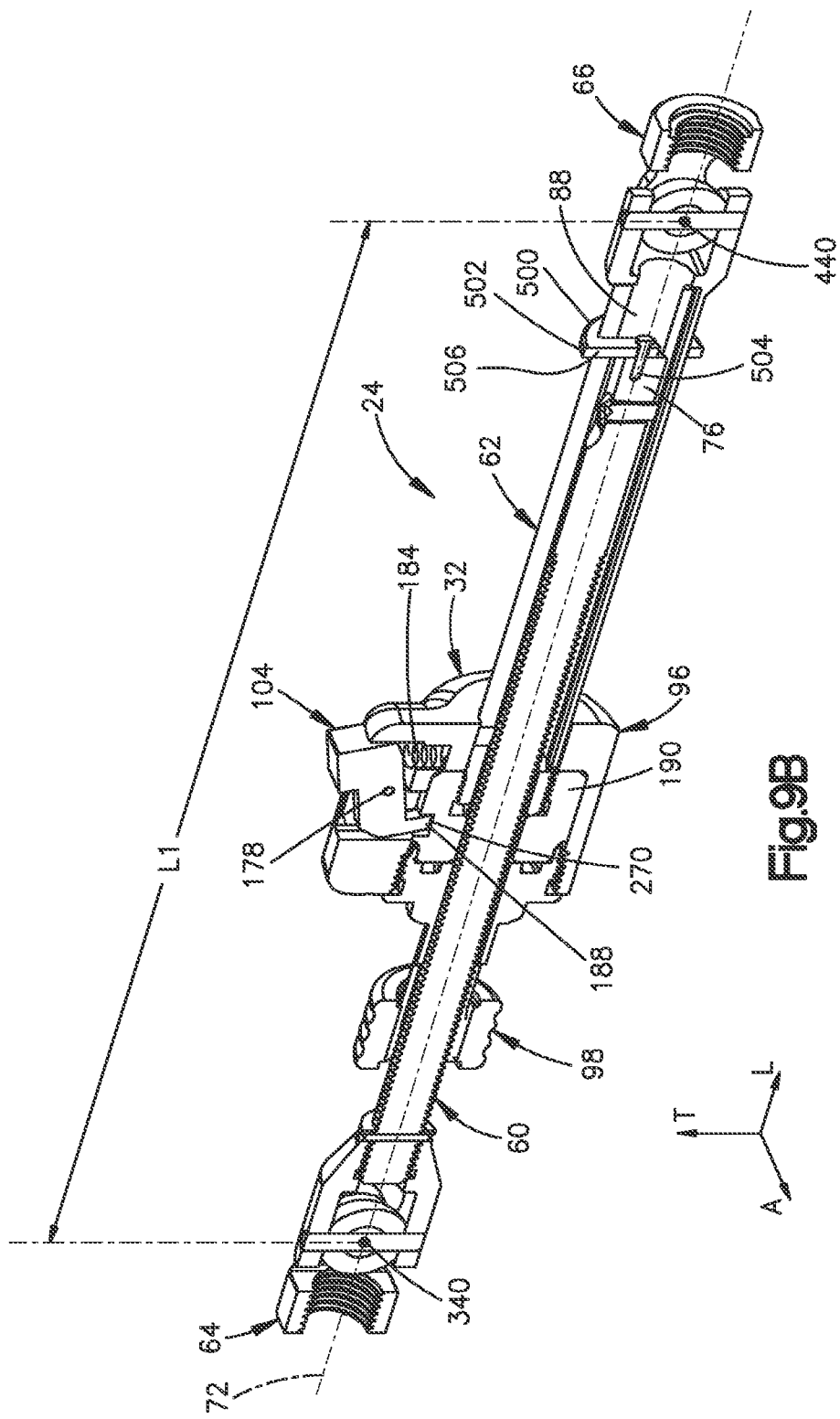
FIG. 9B is a cross-sectional view of the strut illustrated in FIG. 9A.
Figure 10A:
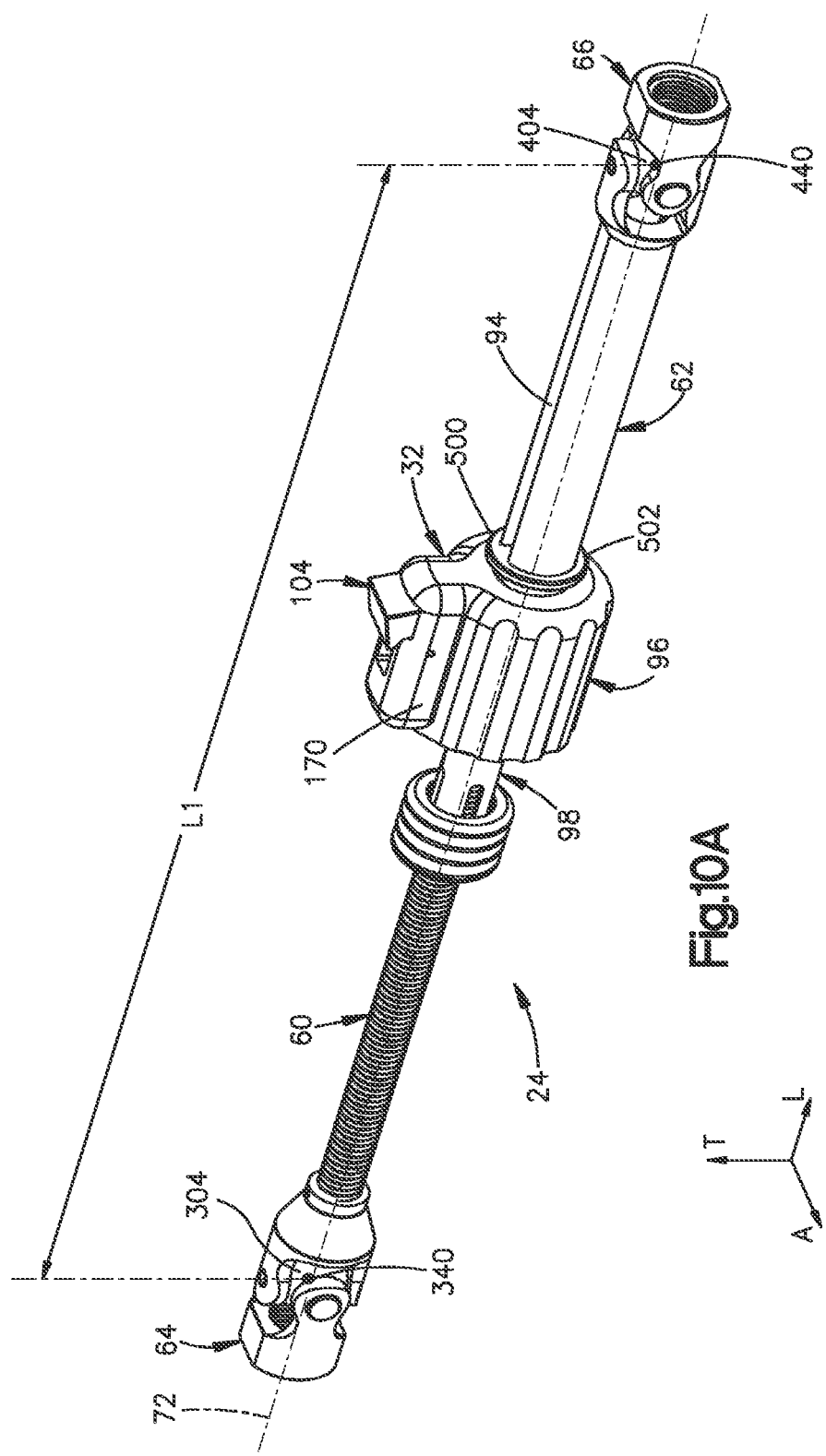
FIG. 10A is a perspective view of the strut illustrated in FIG. 5A, in a second configuration.

Referring to FIGS. 9A to 10B, the strut 24 defines a length L1 measured from a first point on the strut 24 to a second point on the strut 24. As shown in the illustrated embodiment, the length L1 is measured from the cross coupling member 304 of the first joint 64, specifically a center 340 of the cross coupling member 304, along the strut axis 72, to the cross coupling member 404 of the second joint 66, specifically a center 440 of the cross coupling member 404. The length L1 of the strut 24 is adjustable between a minimum length (as shown in FIGS. 9A and 9B) and a maximum length (as shown in FIGS. 10A and 10B). The length L1 is adjustable by actuation of the actuator 32. The actuation of the actuator 32 can include translation along the strut axis 72, rotation about the strut axis 72, or both relative to the threaded rod 60.

To change the length L1 of the strut 24, the locking mechanism 104 is moved from the first, locked configuration to the second unlocked configuration. For example, an applied force is exerted by a user on the base portion 186 of the lever 106. The applied force is greater than the biasing force applied by the spring 184 on the base portion 186, and the applied force is applied in substantially the opposite direction of the biasing force of the spring 184. Application of the applied force as described above pivots the lever 106 about the pivot axis 178. As the lever 106 pivots about the pivot axis 178, the stop portion 188 of the lever 106 moves out of engagement with the recess 270 of the bearing 190. When the stop portion 188 is removed from the recess 270, the locking mechanism 104 is in the second, unlocked configuration and the actuator 32 is now rotatable relative to the threaded rod 60 about the strut axis 72.

Once the actuator 32 has been rotated in a first direction, for example counter-clockwise, such that the stop portion 188 of the lever 106 is no longer aligned with the recess 270, the applied force can be removed from the base portion 186. A torque applied to the gripping member 100, for example to the projection 166, in one embodiment specifically to one of the projection side walls 170, rotates the actuator relative to the threaded rod 60. Because the actuator 32 is translationally coupled to the outer surface, rotation of the actuator 32 translates the threaded rod 60 relative to the actuator 32 and the sleeve 62 changing the length L1 as measured between the cross coupling members 304 and 404 of the first and second joints 64 and 66.

Upon the completion of a full rotation (360 degrees) about the strut axis 72, the stop portion 188 of the lever 106 moves into alignment with the recess 270 of the bearing 190. Once the stop portion 188 and recess 270 are aligned, the biasing force of the spring 184 pivots the lever 106 about the pivot axis 178 until the stop portion 188 is at least partially received within the recess 270. When the stop portion 188 is at least partially received within the recess 270 the locking mechanism 104 is once again in the first, locked configuration and further rotation of the actuator 32 relative to the threaded rod 60 about the strut axis 72 is prevented by interference between the stop portion 188 and the locking feature 268. In one embodiment, the stop portion 188 and the locking feature 268 include opposed surfaces, for example first and second surfaces. The opposed surfaces are configured such that no amount of torque applied by hand to the locking mechanism 104 about the strut axis 72 will cause the opposed surfaces to cam over one another.

In one embodiment, the opposed surfaces are planar and substantially parallel to one another. In another embodiment the opposed (first and second) surfaces are substantially perpendicular to the strut axis. As the locking mechanism 104 rotates back into the first, locked configuration an audible indication, for example a "click" is produced to alert a user to the completion of a revolution of the actuator 32 and confirm that the locking mechanism 104 is once again in the first, locked configuration. In another embodiment, as the locking mechanism 104 rotates back into the first, locked configuration a visual indication, a tactile indication, or both are produced, either instead of or in addition to the audible indication, to alert a user to the completion of a revolution of the actuator 32 and confirm that the locking mechanism 104 is once again in the first, locked configuration.

As shown, the locking mechanism 104 is configured such that the biasing force of the spring 184 is applied to the base portion 186 in a direction that is angularly offset from the direction of elongation of the strut 24, or the strut axis 72 in the illustrated embodiment. The angular offset of the biasing force relative to the strut axis 72, shown in the illustrated embodiment, prevents the application of a torque to the actuator 32 from rotating the actuator 32 relative to the threaded rod 60 when the locking mechanism 104 is in the first, locked configuration. Thus, in the illustrated embodiment, only when the locking mechanism 104 is in the second, unlocked configuration does the application of a torque to the actuator 32 rotate the actuator 32 relative to the threaded rod 60.

The strut 24 is configured such that a single rotation (360 degrees) of the actuator 32 relative to the threaded rod 60, translates the threaded rod 60 a predetermined amount relative to the sleeve 62. Thus a single rotation of the actuator 32 relative to the threaded rod 60, changes the length L1 a predetermined amount. The predetermined amount can be adjusted, for example by selecting a pitch for the corresponding threads of the actuator 32 and the threaded rod 60. In one embodiment, a single rotation of the actuator 32 relative to the threaded rod 60, changes the length L1 of the strut 24 by 1 millimeter (mm).

Referring to FIGS. 6A-6B to 9A-10B, in one embodiment the strut 24 includes a length indicator 500. The length indicator 500 is configured to provide a visual indication of the length L1 of the strut 24. As shown in the illustrated embodiment the length indicator 500 includes a clip 502 that is configured to be coupled to the threaded rod 60 such that clip 502 is translationally secured relative to the threaded rod 60 and rotatable about the strut axis 72 relative to the threaded rod 60. The length indicator 500 can include a pin 504, such that the clip 502 is configured to be attached by the pin 504 to the rod distal end 76. The clip 502 can include a post 506 that extends at least partially through the slot 94 of the sleeve 62 when the clip is attached to the threaded rod 60 and the threaded rod 60 is positioned at least partially within the bore 88 of the sleeve 62. The length indicator 500 can further include markings 508 (as shown in FIG. 9A) on the sleeve outer surface 92. The markings 508 can be configured such that as the threaded rod 60 translates within the bore 88 of the sleeve 62, the clip 502 which is attached to the threaded rod 60, is positioned adjacent a marking that indicates the current length L1 of the strut 24.

Referring to FIGS. 1A-2B and 5A-6B, in one embodiment, the device 20 is configured such that when one of the first and second end portions 26 and 28 of the strut 24 is attached to one of the bases 22 the strut 24 is rotatable about the strut axis 72 relative to the attached base 22, for example a hole 50 of the attached base 22. In another embodiment, the device 20 is configured such that when the first end portion 26 is attached to one of the bases 22, and the second end portion 28 is attached to another of the bases 22, the strut 24 is rotationally locked relative to the bases 22, such that the strut is not rotatable about the strut axis 72 relative to the attached base 22, for example a hole 50 of the attached base 22.

In one embodiment, the device 20 includes the strut 24 having the first joint 64, the second joint 66, and the length L1 measured from the first joint 64 to the second joint 66 along a strut axis 72. The first and second joints 64 and 66 defining first and second fastener receiving holes 350 and 450 respectively, that are each configured to receive a fastener 14 that is configured to secure the strut 24 to a base 22. The strut 24 includes the actuator 32 configured to adjust the length L1, and a locking mechanism 104. The locking mechanism is configured to be supported by the actuator 32, and the locking mechanism 104 includes a locked configuration in which the actuator 32 is prevented from adjusting the length L1, and an unlocked configuration in which the actuator 32 is able to adjust the length L1.

The device 20 further can include first and second external bone fixation members, such as bases 22a and 22b. Each of the first and second external bone fixation members includes a first side wall 44 (or an inner surface) and a second side wall 46 (or an outer surface) that is opposite the first side wall 44. The first side wall 44 defines a space configured to receive the bone 2. The first and second bases 22 each further include a top (or first) surface 38 and a bottom (or second) surface 40 that each extends between the respective first and second side walls 44 and 46. The bases 22 each further including a hole 50 extending from the top surface 38 to the bottom surface 40, the hole 50 configured to receive a fastener 14 to attach the strut 24 to the base 22. The first side wall 44 defines an opening 48 configured to receive the bone 2, and the base 22 defines a center 49 and a radial outward direction that extends from the center 49 to the hole 50 ("fastener receiving hole") that receives a fastener 14 to attach the strut 24 to the base 22.

A method of assembling the external bone fixation device 20 according to any of the embodiments disclosed herein is described below. The strut 24 can be positioned relative to the first external bone fixation member (for example the first base 22a) such that the fastener receiving hole 350 of the first joint 64 is aligned with the fastener receiving hole 50 of the first base 22a. A first fastener 14 is inserted into and at least partially through the fastener receiving hole 350 of the first joint 64 and the fastener receiving hole 50 of the first base 22a, such that at least a portion of the strut 24, for example the actuator 32, is rotatable about the strut axis 72 relative to the fastener receiving hole 50 of the first base 22a. The actuator 32 can be rotated about the strut axis 72 relative to the fastener receiving hole 50 of the first base 22a such that the locking mechanism 104 is spaced from the strut axis 72 in a radially outward direction (a direction from the center 49 to the fastener receiving hole 50 of the first base 22a). In other words at least a portion of the strut 24, for example the actuator 32, is rotated such that the locking mechanism 104 faces outward from the opening 48 and the bone 2. The strut 24 is positioned relative to the second external bone fixation member (for example the base 22b) such that the fastener receiving hole 450 of the second joint 66 is aligned with the fastener receiving hole 50 of the second base 22b. A second fastener 14 is inserted into and at least partially through the fastener receiving hole 450 of the second joint 66 and the fastener receiving hole 50 of the second base 22b. Wherein after both of the fasteners 14 have been inserted into the respective fastener receiving holes, the portion of the strut 24, for example the actuator 32, is not rotatable relative to the fastener fixation hole 50 of the first base 22a about the strut axis 72 when the locking mechanism 104 is in the locked configuration.

In another embodiment, the method of assembling the external bone fixation device 20 according to any of the embodiments disclosed herein includes, positioning the strut 24 relative to the second external bone fixation member (for example the second base 22b) such that the fastener receiving hole 350 of the first joint 64 is aligned with the fastener receiving hole 50 of the second base 22b. A first fastener 14 is inserted into and at least partially through the fastener receiving hole 350 of the first joint 64 and the fastener receiving hole 50 of the second base 22b, such that at least a portion of the strut 24, for example the actuator 32, is rotatable about the strut axis 72 relative to the fastener receiving hole 50 of the second base 22b. The actuator 32 can be rotated about the strut axis 72 relative to the fastener receiving hole 50 of the second base 22b such that the locking mechanism 104 is spaced from the strut axis 72 in a radially outward direction (a direction from the center 49 to the fastener receiving hole 50 of the second base 22b). In other words at least a portion of the strut 24, for example the actuator 32, is rotated such that the locking mechanism 104 faces outward from the opening 48 and the bone 2. The strut 24 is positioned relative to the first external bone fixation member (for example the base 22b) such that the fastener receiving hole 450 of the second joint 66 is aligned with the fastener receiving hole 50 of the first base 22a. A second fastener 14 is inserted into and at least partially through the fastener receiving hole 450 of the second joint 66 and the fastener receiving hole 50 of the first base 22a. Wherein after both of the fasteners 14 have been inserted into the respective fastener receiving holes, the portion of the strut 24, for example the actuator 32, is not rotatable relative to the fastener fixation hole 50 of the second base 22b about the strut axis 72 when the locking mechanism 104 is in the locked configuration.

In another embodiment, the method of assembling the external bone fixation device 20 according to any of the embodiments disclosed herein includes, positioning the strut 24 relative to one of the external bone fixation member (for example the first base 22a) such that the fastener receiving hole 450 of the second joint 66 is aligned with the fastener receiving hole 50 of the first base 22a. The actuator 32 can be rotated about the strut axis 72 relative to the fastener receiving hole 50 of the first base 22a such that the locking mechanism 104 is spaced from the strut axis 72 in a radially outward direction (a direction from the center 49 to the fastener receiving hole 50 of the first base 22a). In other words at least a portion of the strut 24, for example the actuator 32, is rotated such that the locking mechanism 104 faces outward from the opening 48 and the bone 2. A first fastener 14 is inserted into and at least partially through the fastener receiving hole 450 of the second joint 66 and the fastener receiving hole 50 of the first base 22a, such that at least a portion of the strut 24, for example the actuator 32, is not rotatable about the strut axis 72 relative to the fastener receiving hole 50 of the first base 22a when the locking mechanism 104 is in the locked configuration. A second fastener 14 is inserted into and at least partially through the fastener receiving hole 350 of the first joint 66 and the fastener receiving hole 50 of the second base 22b.

In another embodiment, the method of assembling the external bone fixation device 20 according to any of the embodiments disclosed herein includes, positioning the strut 24 relative to one of the external bone fixation member (for example the second base 22b) such that the fastener receiving hole 450 of the second joint 66 is aligned with the fastener receiving hole 50 of the second base 22b. The actuator 32 can be rotated about the strut axis 72 relative to the fastener receiving hole 50 of the second base 22b such that the locking mechanism 104 is spaced from the strut axis 72 in a radially outward direction (a direction from the center 49 to the fastener receiving hole 50 of the second base 22b). In other words at least a portion of the strut 24, for example the actuator 32, is rotated such that the locking mechanism 104 faces outward from the opening 48 and the bone 2. A first fastener 14 is inserted into and at least partially through the fastener receiving hole 450 of the second joint 66 and the fastener receiving hole 50 of the second base 22b, such that at least a portion of the strut 24, for example the actuator 32, is not rotatable about the strut axis 72 relative to the fastener receiving hole 50 of the second base 22b when the locking mechanism 104 is in the locked configuration. A second fastener 14 is inserted into and at least partially through the fastener receiving hole 350 of the first joint 66 and the fastener receiving hole 50 of the first base 22a.

In one embodiment the external bone fixation device 20 includes a kit having a plurality of struts 24 and a plurality of bases 22. The kit can further include a plurality of attachment mechanisms 200. In another embodiment, the plurality of struts 24 includes struts with different minimum and maximum lengths L1 (measured, for example, from the center 340 of the cross coupling member 304 of the first joint 64 to the center 440 of the cross coupling member 440 of the second joint 66). The plurality of struts 24 in the kit, in one embodiment, can include any combination of one or more extra short struts, one or more short struts, one or more medium struts, and one or more long struts. In another embodiment the extra short struts define a minimum length L1 of about 91 mm and a maximum length L1 of about 121 mm for a total travel distance of about 30 mm. In another embodiment the short struts define a minimum length L1 of about 116 mm and a maximum length L1 of about 152 mm for a total travel distance of about 36 mm. In another embodiment the medium struts define a minimum length L1 of about 142 mm and a maximum length L1 of about 205 mm for a total travel distance of about 63 mm. In another embodiment the long struts define a minimum length L1 of about 195 mm and a maximum length L1 of about 311 mm for a total travel distance of about 116 mm.

The plurality of bases 22 in the kit, in one embodiment, can include any combination of one or more bases with an outer diameter of 90 mm, 120 mm, 150 mm, 180 mm, 210 mm, and 240 mm. The plurality of attachment mechanisms 200 in the kit, in one embodiment, can include any combination of one or more brackets 202, fasteners 206, wires 208 and rods 210.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure as defined by the claims.

What is claimed is:

1. A method of assembling an external bone fixation device, the method comprising the steps of:
   positioning a strut relative to a first external bone fixation member such that a fastener receiving hole of a first joint of the strut is aligned with a fastener receiving hole of the first external bone fixation member;
   inserting a fastener into and at least partially through the fastener receiving hole of the first joint and the fastener receiving hole of the first external bone fixation member;
   rotating the strut relative to the fastener receiving hole of the first external bone fixation member about a strut axis, which the strut is elongate along, until a locking mechanism of the strut is spaced from the strut axis in a radial outward direction which extends from a center of the first external bone fixation member to the fastener receiving hole of the first external bone fixation member;
   positioning the strut relative to a second external bone fixation member such that a fastener receiving hole of a second joint of the strut is aligned with a fastener receiving hole of the second external bone fixation member;

inserting a second fastener into and at least partially through the fastener receiving hole of the second joint and the fastener receiving hole of the second external bone fixation member;

wherein after the step of inserting the second fastener into and at least partially through the fastener receiving holes of the second joint and the second external bone fixation member, an actuator of the strut is not rotatable relative to the fastener receiving hole of the first external bone fixation member about the strut axis when the locking mechanism of the strut is in a locked configuration in which the actuator is prevented from adjusting a length of the strut measured from the first joint to the second joint along the strut axis.

2. The method of claim 1, further comprising the steps of:

positioning a second strut relative to the first external bone fixation member such that a fastener receiving hole of a first joint of the second strut is aligned with a second fastener receiving hole of the first external bone fixation member;

inserting a third fastener into and at least partially through the fastener receiving hole of the first joint of the second strut and the second fastener receiving hole of the first external bone fixation member;

rotating the second strut relative to the second fastener receiving hole of the first external bone fixation member about a second strut axis, which the second strut is elongate along;

positioning the second strut relative to the second external bone fixation member such that a fastener receiving hole of a second joint of the second strut is aligned with a second fastener receiving hole of the second external bone fixation member;

inserting a fourth fastener into and at least partially through the fastener receiving hole of the second joint of the second strut and the second fastener receiving hole of the second external bone fixation member;

wherein after the step of inserting the fourth fastener into and at least partially through the fastener receiving hole of the second joint of the second strut and the second fastener receiving hole of the second external bone fixation member, an actuator of the second strut is not rotatable relative to the second fastener receiving hole of the first external bone fixation member about the second strut axis when a locking mechanism of the second strut is in a locked configuration in which the actuator of the second strut is prevented from adjusting a length of the second strut measured from the first joint of the second strut to the second joint of the second strut along the second strut axis.

3. The method of claim 2, wherein the step of rotating the second strut includes rotating the second strut until the locking mechanism of the second strut is spaced from the second strut axis in the radial outward direction.

4. A method of adjusting a length of a strut body of a strut from a first joint to a second joint that is spaced from the first joint along an axis, wherein the first joint is carried by a threaded rod of the strut body and is attached to a first external bone fixation member, and the second joint is carried by a sleeve of the strut body and is attached to a second external bone fixation member, the method comprising the steps of:

applying a force to a locking mechanism of the strut along a direction offset with respect to the strut axis, so as to iterate the locking mechanism from a locked configuration to an unlocked configuration, whereby when the locking mechanism is in the locked configuration, an actuator of the strut, that is configured to rotate relative to the strut body so as to cause the strut body to change in length, is rotatably fixed to the strut body, and when the locking mechanism is in the unlocked configuration, the actuator is rotatable with respect to the strut body; and after the applying step, rotating the actuator of the strut about the strut axis relative to the strut body, thereby causing at least one of the threaded and the sleeve of the strut body to translate relative to the other of the threaded rod and the sleeve along the strut axis.

5. The method of claim 4, wherein the moving step includes the step of pivoting the locking mechanism about a pivot axis.

6. The method of claim 5, wherein the pivoting step includes the step of applying a force to the locking mechanism in a direction that is offset with respect to both the strut axis and the pivot axis.

7. The method of claim 6, wherein the applying step includes the step of removing a portion of the locking mechanism from a recess of the strut, and the rotating step is performed after the applying step.

8. The method of claim 7, wherein the applying step includes the step of compressing a spring.

9. The method of claim 8, further comprising the step of removing the force from the locking mechanism thereby allowing the spring to expand, wherein the removing step is performed after the rotating step.

10. The method of claim 9, further comprising a second step of rotating the actuator of the strut relative to the strut body about the strut axis, thereby causing at least one of a threaded rod of the strut body and a sleeve of the strut body to translate relative to the other of the sleeve and the threaded rod along the strut axis, wherein the second rotating step is performed after the removing step.

11. The method of claim 10, wherein the first rotating step includes rotating the actuator of the strut relative to the strut body about the strut axis in a first direction, and the second rotating step includes rotating the actuator of the strut relative to the strut body about the strut axis in the first direction.

12. The method of claim 11, further comprising the step of aligning the portion of the locking mechanism with the recess thereby allowing the spring to expand and bias the portion of the locking mechanism into the recess.

13. The method of claim 12, wherein the aligning step includes the spring biasing the portion of the locking mechanism into the recess thereby producing an audible indication.

14. The method of claim 12, wherein the aligning step includes the step of moving a surface of the portion to face a surface of the strut that partially defines the recess such that no amount of torque applied by hand to the locking mechanism about the strut axis will cause the surface of the portion and the surface of the strut to cam over one another.

15. A method of assembling an external bone fixation device configured to repair a deformity in a bone, the external bone fixation device including: (1) a strut having a first joint, a second joint, and a length measured from the first joint to the second joint along a strut axis, the first and second joints defining first and second fastener receiving holes respectively, the strut further including an actuator configured to adjust the length, and a locking mechanism configured to be supported by the actuator, the locking mechanism including a locked configuration in which the actuator is prevented from adjusting the length, and an unlocked configuration in which the actuator is able to adjust the length; and (2) first and second external bone fixation members, each of the first and second external bone fixation members including a top surface and a bottom surface that each extends between the respective inner and outer surfaces, the first and second external fixation members each further including a fastener receiving hole extending from the top surface to the bottom surface, wherein the first external fixation member defines a center and a radial outward direction that extends from the center to the fastener receiving hole of the first external bone fixation member, the method comprising:

positioning the strut relative to the first external bone fixation member such that the fastener receiving hole of the first joint is aligned with the fastener receiving hole of the first external fixation member;

inserting a first fastener into and at least partially through the fastener receiving hole of the first joint and the fastener receiving hole of the first external bone fixation member;

rotating the actuator about the strut axis relative to the fastener receiving hole of the first external bone fixation member such that the locking mechanism is spaced from the strut axis in the radial outward direction;

positioning the strut relative to the second external bone fixation member such that the fastener receiving hole of the second joint is aligned with the fastener receiving hole of the second external bone fixation member;

inserting a second fastener into and at least partially through the fastener receiving hole of the second joint and the fastener receiving hole of the second external bone fixation member;

wherein after the step of inserting the second fastener into and at least partially through the fastener receiving holes of the second joint and the second external bone fixation member, the actuator is not rotatable relative to the fastener receiving hole of the first external bone fixation member about the strut axis when the locking mechanism is in the locked configuration.

16. The method of claim 15, wherein the strut is a first strut, the external bone fixation device includes: (1) a second strut having a first joint, a second joint, and a length measured from the first joint of the second strut to the second joint of the second strut along a strut axis of the second strut, the first and second joints of the second strut defining first and second fastener receiving holes respectively, the second strut further including an actuator configured to adjust the length of the second strut, and a locking mechanism configured to be supported by the actuator of the second strut, the locking mechanism of the second strut including a locked configuration in which the actuator of the second strut is prevented from adjusting the length of the second strut, and an unlocked configuration in which the actuator of the second strut is able to adjust the length of the second strut, and the method further includes the steps of:

positioning the second strut relative to the first external bone fixation member such that the fastener receiving hole of the first joint of the second strut is aligned with a second fastener receiving hole of the first external fixation member;

inserting a third fastener into and at least partially through the fastener receiving hole of the first joint of the second strut and the second fastener receiving hole of the first external bone fixation member;

rotating the actuator of the second strut about the strut axis of the second strut relative to the second fastener receiving hole of the first external bone fixation member such that the locking mechanism of the second strut is spaced from the strut axis of the second strut in the radial outward direction;

positioning the strut relative to the second external bone fixation member such that the fastener receiving hole of the second joint is aligned with the fastener receiving hole of the second external bone fixation member;

inserting a second fastener into and at least partially through the fastener receiving hole of the second joint and the fastener receiving hole of the second external bone fixation member;

wherein after the step of inserting the second fastener into and at least partially through the fastener receiving holes of the second joint and the second external bone fixation member, the actuator is not rotatable relative to the fastener receiving hole of the first external bone fixation member about the strut axis when the locking mechanism is in the locked configuration.

* * * * *